United States Patent
Iwahashi et al.

[11] Patent Number: 6,103,193
[45] Date of Patent: Aug. 15, 2000

[54] AUTOMATIC IMMUNOASSAY METHOD AND APPARATUS

[75] Inventors: Kyoichi Iwahashi, Ryugasaki; Toshimi Kawamura, Fussa; Eiji Ikeda, Chiba-ken; Mitsutoshi Sato, Urawa, all of Japan

[73] Assignee: Sanko Junyaku Co., Ltd., Tokyo, Japan

[21] Appl. No.: 09/147,206

[22] PCT Filed: May 1, 1996

[86] PCT No.: PCT/JP96/01194

§ 371 Date: Oct. 28, 1998

§ 102(e) Date: Oct. 28, 1998

[87] PCT Pub. No.: WO97/41437

PCT Pub. Date: Nov. 6, 1997

[51] Int. Cl.[7] .......................... G01N 25/20; G01N 21/00; G01N 35/00; C12M 3/02
[52] U.S. Cl. .................. 422/50; 422/62; 422/63; 422/64; 422/65; 422/99; 422/104; 422/236; 422/312; 422/919; 422/920; 422/936; 435/286.1; 435/286.2; 435/287.1; 435/287.2; 435/288.1; 435/288.2; 435/304.1; 435/809; 436/43; 436/47; 436/48; 436/49
[58] Field of Search ...................... 422/50, 62–65, 422/99, 104, 232, 236, 237, 239, 312, 913, 919, 920, 934, 936, 939, 946; 435/286.1, 286.2, 286.4, 287.1, 287.2, 287.3, 288.1, 288.2, 304.1, 809; 436/810, 43, 47–49

[56] References Cited

U.S. PATENT DOCUMENTS

| | | | |
|---|---|---|---|
| 3,081,158 | 3/1963 | Winter | 23/253 |
| 4,252,897 | 2/1981 | Axford et al. | 435/34 |
| 4,585,623 | 4/1986 | Chandler | 422/57 |
| 4,590,157 | 5/1986 | Chandler et al. | 435/7 |
| 4,665,034 | 5/1987 | Chandler | 435/287 |
| 4,791,060 | 12/1988 | Chandler | 435/296 |
| 4,981,801 | 1/1991 | Suzuki et al. | 435/290 |
| 5,005,981 | 4/1991 | Schulte et al. | 366/219 |
| 5,035,861 | 7/1991 | Grandone | 422/64 |
| 5,104,808 | 4/1992 | Laska et al. | 436/48 |
| 5,128,103 | 7/1992 | Wang et al. | 422/64 |
| 5,164,318 | 11/1992 | Sato et al. | 435/288 |
| 5,183,638 | 2/1993 | Wakatake | 422/64 |
| 5,316,726 | 5/1994 | Babson et al. | 422/65 |
| 5,384,093 | 1/1995 | Ootani et al. | 422/63 |
| 5,453,246 | 9/1995 | Nakayama et al. | 422/63 |
| 5,455,006 | 10/1995 | Aota et al. | 422/63 |
| 5,501,838 | 3/1996 | Ootani et al. | 422/65 |
| 5,736,413 | 4/1998 | Uzan et al. | 436/526 |
| 5,846,491 | 12/1998 | Choperrena et al. | 422/67 |
| 5,849,247 | 12/1998 | Uzan et al. | 422/65 |
| 5,863,754 | 1/1999 | Bajard | 435/39 |
| 5,882,594 | 3/1999 | Kawaguchi et al. | 422/64 |

*Primary Examiner*—Christopher L. Chin
*Assistant Examiner*—Pensee T. Do
*Attorney, Agent, or Firm*—Arent Fox Kintner; Plotkin & Kahn, PLLC

[57] ABSTRACT

An automatic immunoassay method and apparatus which not only permit automatic operations of supplying and discarding reaction tubes, washing for B/F separation, dispensation of reagents, and measurement, but also permit the reaction time to be varied arbitrarily and can cope with any of the assay techniques including one-step and two-step noncompetitive sandwich techniques and competitive techniques. The automatic immunoassay apparatus comprises: a reaction tube turret which turns intermittently at a given speed; a reaction tube holding part provided with inner and outer rows of reaction tube holders on the upper periphery thereof; means for supplying each reaction tube to the reaction tube holding part; means for moving a reaction tube held in one reaction tube holder to another reaction tube holder while skipping over a desired number of reaction tube holders; means for dispensing a specimen to the reaction tube; means for supplying particles to the reaction tube; means for dispensing a labeled reagent to the reaction tube; means for washing to effect B/F separation; means for dispensing an assaying reagent to the reaction tube; means for determining the quantity of labeled substances in the solution after the reaction in the reaction tube; and means for discarding the used reaction tube by taking the same out of the reaction tube holding part.

5 Claims, 22 Drawing Sheets

AUTOMATIC IMMUNOASSAY METHOD AND APPARATUS

TECHNICAL FIELD

This invention relates to an automatic immunoassay and an apparatus for the same which are capable of effectively and automatically performing an immunoassay by the use of an antigen-antibody reaction for an assay of a particular substance in a sample.

BACKGROUND ART

Conventionally known immuno assay using an antigen-antibody reaction include a one step or a two step noncompetitive sandwich method, and a competitive method.

Now, description will be given of an assay embodied in the one step non-competitive sandwich method for assaying the amount of an antigen contained in a sample, such as blood collected from a patient as a test sample. A sample to be assayed is added into a reaction cuvette. The reaction cuvette is previously charged with an antibody (hereinafter referred to as a "solid phase antibody") bound to an insoluble carrier (solid phase) such as the inside surface of a plastics cuvette or plastics particles, and an antibody (hereinafter referred to as "labeled antibody") bound to a labeling substance, such as a radioactive substance, a fluorescent substance, or an enzyme. In the reaction cuvette, an antigen contained in the sample reacts with the solid phase antibody and, as a result of this antigen-antibody reaction (immuno-reaction), an antigen-antibody complex is formed. At the same time, the labeled antibody is combined with the antigen-antibody complex, thus forming a complex composed of three components sandwiched together, namely, the solid phase antibody, antigen and labeled antibody.

Thus, the labeling substance of the labeled antibody is bound to the solid phase with the agency of the antigen in the sample.

Then, a process is performed to separate an excessive labeled antibody which is other than the labeling substance bound to the solid phase and which has not been bound to the antigen added into the reaction cuvette, and antibody components which have not taken part in the immuno-reaction (this operation being hereinafter referred to as "B/F separation"). Finally, the amount of the labeling substance proportional to the amount of the antigen bound to the solid phase is quantitatively assayed by a physical or a chemical technique by making use of properties of the labeling substance, thereby to determine the antigen concentration in the sample.

On the other hand, the two-step non-competitive sandwich method is an assay of the class wherein to a reaction cuvette previously charged with a solid phase antibody alone, a sample is added to perform a first reaction, and after that a labeled antibody is added into the reaction cuvette so as to perform a second reaction.

In other words, the sample is added into the reaction cuvette which is previously charged with the solid phase antibody (or a reagent containing therein the solid phase antibody). As a consequence, a particular antigen in the sample is bound and fixed to an insoluble carrier via an immuno-reaction with the solid phase antibody. Unreacted components that have caused no immuno-reaction are removed from the reaction cuvette through the B/F separation. Then, the labeled antibody is added into the reaction cuvette to cause an immuno-reaction through which a complex consisting of the solid phase antibody, the antigen, and the labeled antibody is formed. Unreacted components and residue are removed from the reaction cuvette via the B/F separation.

The foregoing operation is followed by an assay in which the amount of the complex bound to the insoluble carrier is assayed by quantitative determination of the amount of the labeling substance in the same manner as the aforesaid one-step method, so as to determine the antigen concentration of the sample.

Apart from the noncompetitive sandwich methods, the so-called competitive method is also known in which an antigen (generally referred to as "labeled antigen") which is labeled in advance with a labeling substance, and an antigen in a sample are competitively reacted with the aforesaid solid phase antibody.

According to the competitive method, the sample is put into reaction with the solid phase antibody and a reagent containing the labeled antigen. A component in the sample to be assayed (i.e., an antigen) and the labeled antigen take part in a competitive reaction with an immuno reactive portion of the solid phase antibody. As a result of this reaction, an unknown amount of antigen component contained in the sample and a predetermined amount of labeled antigen component, respectively, form immune complexes according to their ratio of amount (or ratio of concentration). Then, unreacted components and residue are removed by the B/F separation in the same manner as the sandwich method, and after that the amount of the labeling substance bound to the solid phase is assayed by quantitative determination using the properties of the labeling substance with the result that the amount of the antigen in the sample can be determined by calculation made in accordance with the ratio described above.

As previously described, assays of the amount of the labeling substance bound and fixed to the solid phase are differentiated by the properties of the labeling substance (may be also called "marker"). According to the classification prepared on the basis of this point of view, the immunoassay is frequently called, in an abbreviated form, "FIA" when involving the use of a fluorescent substance, "RIA" when involving the use of a radioactive substance, "EIA" when involving the use of an enzyme substance and "CLIA" when involving the use of a chemiluminescent substance as a labeling substance, respectively.

In the immunoassay of the type concerned a means is used for forming an immobilized solid phase. This means may include an antibody- or antigen-insolubilized carrier consisting of an antibody or an antigen fixed to tiny balls of synthetic resin such as polystyrene or polyvinyl chloride, tiny iron balls, tiny glass balls or tiny glass flakes (such a carrier is generally called "beads" or "particles", but in the description given below, the term "particles" is used to refer to the carrier).

In the aforesaid assays, an operation for supplying/discarding particles in the reaction cuvette, an operation for performing a washing for B/F separation, and an operation for replacing the particles should be performed at a predetermined timing. This requirement is too strict for the manual operations, and so various proposals for automated assays have been made (Japanese Patent Laid-open Publication No. 62-133355, Japanese Patent Laid-open Publication No. 62-133356, Japanese Patent Laid-open Publication No. 63-24160, Japanese Patent Laid-open Publication No. 63-24161, and Japanese Patent Laid-open Publication No. 3-51762). These prior proposals are, however, not fully satisfactory in terms of the way of timing.

The present invention was conceived in view of the foregoing prior art and has for its object the provision of an automatic immunoassay and an apparatus for the same which are capable of automatically performing a series of operations necessary for supplying and discarding particles in a reaction cuvette, for performing a washing for the B/F separation, for dispensing a reagent, and for performing an immunoassay, while allowing the reaction time to be changed freely, and which are readily practiced and embodied in the one step or the two step noncompetitive sandwich method as well as the competitive method.

DISCLOSURE OF THE INVENTION

To solve the foregoing problems, an apparatus for an automatic immunoassay of the present invention is characterized by comprising: a reaction tube turret intermittently rotatable at a predetermined speed; a reaction tube holding portion including a plurality of reaction tube holders arranged in two rows composed of an inner raw and an outer raw along the periphery of an upper surface of said reaction tube turret; a reaction tube supplying means for supplying a reaction tube to said reaction tube holding portion; a reaction tube transfer means for transferring the reaction tube held by one of said reaction tube holders to another reaction tube holder while skipping a desired number of reaction tube holders; a sample dispensing means for dispensing a sample to the reaction tube; a particle supplying means for supplying particles to the reaction tube; a reagent dispensing means for dispensing a labeled reagent to the reaction tube; a washing means for performing a B/F separation; an assaying reagent dispensing means for dispensing an assaying reagent to the reaction tube; an assaying means for assaying the amount of the labeling substance in a reacted reaction solution in the reaction tube; and a reaction tube discarding means for removing the assayed reaction tube from said reaction tube holding portion and discarding the thus removed reaction tube.

An automatic immunoassay of the present invention is characterized by using the apparatus for the automatic immunoassay specified above, and transferring the reaction tube to a predetermined position on said reaction tube holding portion according to a reaction time.

In one preferred form, the invention provides an automatic immunoassay characterized by using the apparatus for the automatic immunoassay set forth above and comprising the steps of: supplying a reaction tube by said reaction tube supplying means to a reaction tube holder of an inner one of said two rows of reaction tube holders on the reaction tube turret, with the reaction tube holding therein a sample previously supplied; supplying particles into said reaction tube by the particle supplying means; letting said sample and said particles perform a first antigen-antibody reaction for a predetermined period of time; after said first reaction is completed, washing said particles sufficiently to perform a B/F separation; dispensing a labeled reagent into the reaction tube by said reagent dispensing means; letting said sample, said particles and said labeled reagent perform a second antigen-antibody reaction for a predetermined period of time; after said second reaction is completed, washing said particles sufficiently to perform the B/F separation; dispensing an assaying reagent into the reaction tube; assaying the amount of the labeling substance in a reacted reaction solution in the reaction tube; and discarding the assayed reaction tube, wherein in order to set a reaction time of said first reaction at said predetermined period of time, the reaction tube is transferred by the reaction tube transfer means to one reaction tube holder in said inner row while skipping a desired number of reaction tube holders, and wherein in order to set a reaction time of said second reaction at said predetermined period of time, the reaction tube is transferred by the reaction tube transfer means to one reaction tube holder in said outer row while skipping a desired number of reaction tube holders. This method describes the way of practicing the apparatus of this invention in the two step noncompetitive sandwich method.

In another preferred form, the present invention provides an automatic immunoassay characterized by using the automatic immunoassay apparatus set forth above and comprising the steps of: supplying a reaction tube by said reaction tube supplying means to a reaction tube holder in an outer one of said two rows of reaction tube holders on the reaction tube turret, with the reaction tube holding therein a sample previously supplied; supplying particles into said reaction tube by the particle supplying means; dispensing a labeled reagent into the reaction tube by said reagent dispensing means; letting said sample, said particles and said labeled reagent perform an antigen-antibody reaction for a predetermined period of time; after said reaction is completed, washing said particles sufficiently to perform the B/F separation; dispensing an assaying reagent into the reaction tube; assaying the amount of the labeling substance in a reacted reaction solution in the reaction tube; and discarding the assayed reaction tube, wherein in order to set a reaction time of said reaction at said predetermined period of time, the reaction tube is transferred by the reaction tube transfer means to one reaction tube holder in said outer row while skipping a desired number of reaction tube holders. In one alternative form, the reaction tube may be first supplied to the reaction tube holder of the inner row, and after that in performing a skip-transfer operation for setting the reaction time, the reaction tube is transferred to a predetermined one of the reaction tube holders of the inner row. As a further alternative, it is possible to firstly supply the reaction tube to the reaction tube holder of the inner row, and then transfer the reaction tube to a predetermined one of the reaction tube holders of the outer row when a skip-transfer operation for setting the reaction time is performed. The foregoing method describes the way of practicing the apparatus of this invention in the one step noncompetitive sandwich method. The same practicing technique is also applicable when the competitive method is to be performed.

In any of the automatic immunoassay described above, the step of supplying a reaction tube by said reaction tube supplying means to a reaction tube holder in said inner row on the reaction tube turret, with the reaction tube holding therein a sample previously supplied, may be replaced by a step of supplying a reaction tube to a reaction tube holder in said inner row on the reaction tube turret, and a step of supplying a sample into the thus supplied reaction tube. In the case where the sample dispensing operation and the particle dispensing operation are performed on the reaction tube turret, the last-mentioned two operations may be performed in any sequence. No particular problem arises from their processing sequence.

The present invention makes it possible to set the reaction time by a flexible use of the reaction tube holding portion arranged on the reaction tube turret in the form of two rows (inner and outer circular rows) of reaction tube holders. In setting the reaction time, the number of reaction tube holders provided in each row on the reaction tube turret is used to determine a desired arrival position for the reaction tubes to be skip-transferred by the reaction tube transfer means. This makes it possible to set various reaction times with high degree of flexibility. In addition, the present invention can be practiced and embodied, with no particular difficulty, in various different assaying techniques including the one step or two step noncompetitive sandwich method, and the competitive method.

BEST MODE FOR CARRYING OUT THE INVENTION

One embodiment of the present invention will be described below with reference to the accompanying drawings.

Figure 1:
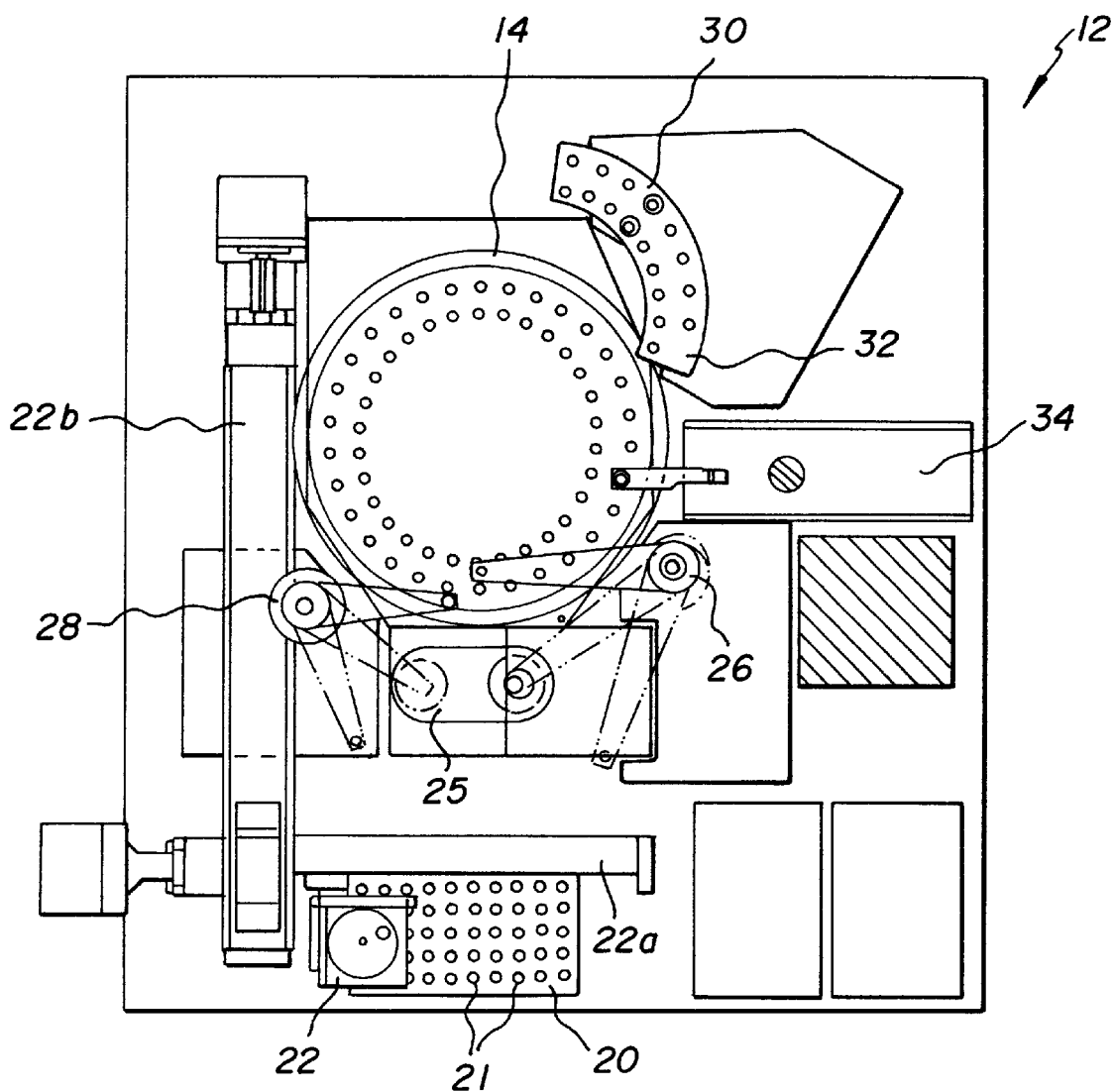
FIG. 1 is a top plan view showing one embodiment of an apparatus for an automatic immunoassay according to the present invention.
Figure 2:
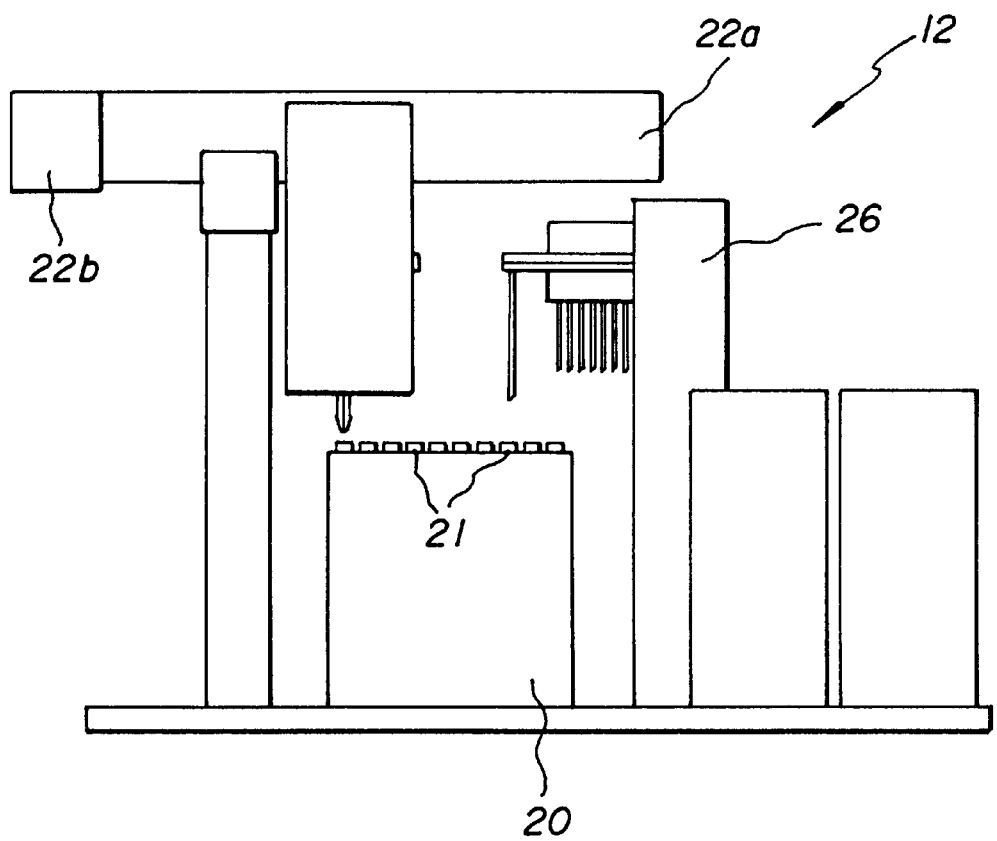
FIG. 2 is a side view of FIG. 1.
Figure 3:
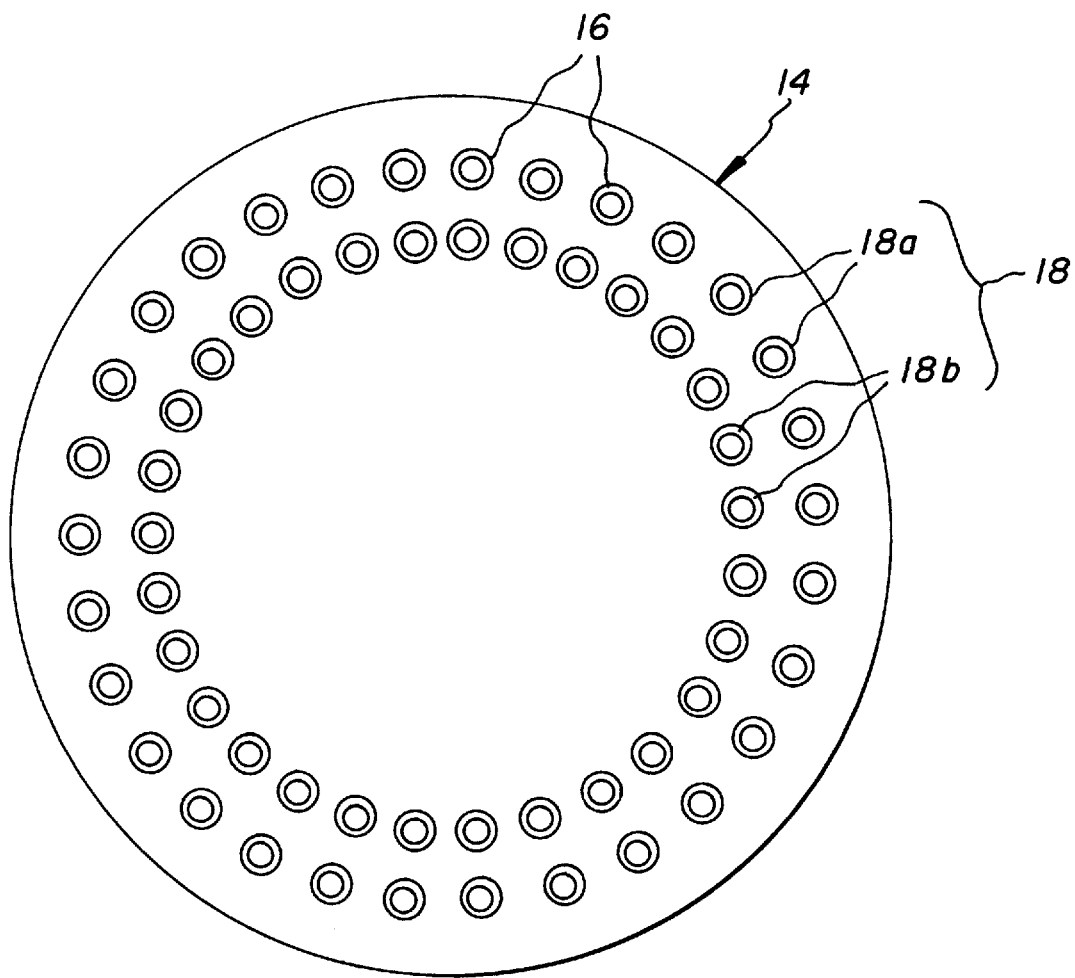
FIG. 3 is a top plan view showing only a reaction tube turret.
Figure 4:
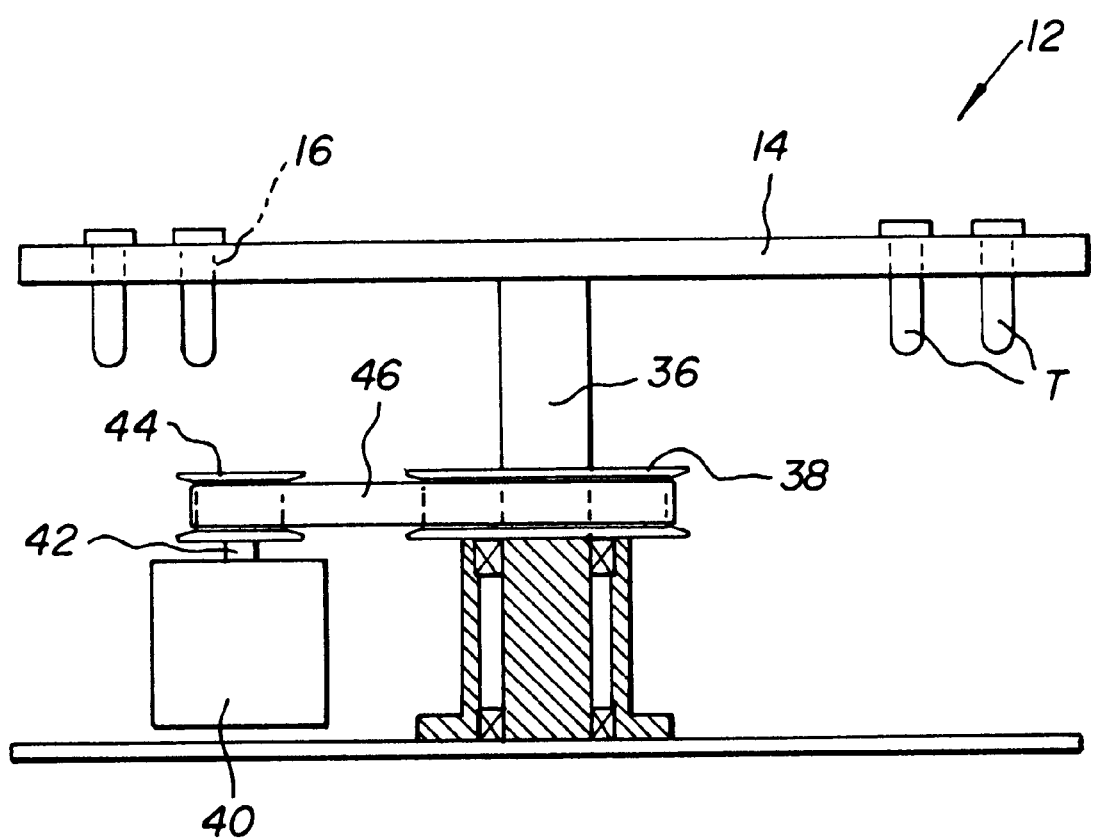
FIG. 4 is a side view, partly in cross section, of a drive mechanisms for the reaction tube turret.

FIG. 1 is a top plan view showing one embodiment of an apparatus for an automatic immunoassay according to the present invention. FIG. 2 is a side view of FIG. 1. FIG. 3 is a top plan view showing only a reaction tube turret. FIG. 4 is a side view, partly in cross section, of a drive mechanisms for the reaction tube turret.

In FIG. 1, reference numeral 12 denotes an apparatus for an automatic immunoassay of the present invention, including a reaction tube turret 14 intermittently rotatable at a predetermined speed. The reaction tube turret 14 has formed in its upper surface along the periphery thereof a plurality of reaction tube holders 16 arranged in two concentrical circular rows, namely an inner row 18a of reaction tube holders and an outer row 18b of reaction tube holders, so as to jointly form a reaction tube holding portion 18. The number of reaction tube holders 16 provided in the upper surface of the reaction tube turret 14 may be determined in an appropriate manner according to the mode of reaction performed. In the case of the embodiment shown in FIG. 1, the inner row 18a and the outer row 18b each have thirty reaction tube holders 16 and, hence, a total of sixty reaction tube holders 14 is provided.

Reference numeral 20 denotes a reaction tube rack provided with a great multiplicity of retainer portions 21 for holding therein the reaction tubes T. Designated by 22 is a reaction tube transfer means which is composed of an X-axis transfer mechanism 22a and a Y-axis transfer mechanism 22b. The reaction tube transfer means 22 performs the function of transferring the individual reaction tube T held in the retaining portions 21 of the reaction tube rack 20 to the reaction tube holders 16 and also transferring the reaction tube T held in one reaction tube holder 16 to another reaction tube holder 16 while skipping a desired number of reaction tube holders 16. In this instance, the reaction tube T held in the reaction tube holder 16 of the inner row 18a or the outer row 18b may be transferred to another reaction tube holder 16 in the same row 18a or 18b, or alternatively to another reaction tube holder 16 in the other row 18b or 18a. The reaction tube transfer means 22 includes a reaction tube supplying means for supplying the reaction tubes T to the reaction tube holding portion 18, and a reaction tube discarding means for removing the assayed reaction tubes T from the reaction tube holding portion 18 and discarding the removed reaction tubes T.

Reference numeral 26 denotes a particle supplying means for supplying particles to the reaction tubes T, the particle supplying means 26 being provided on a reagent table 25. Designated by 28 is a reagent dispensing means for dispensing a labeled reagent into the reaction tubes T. Numeral 30 denotes a washing means for performing the B/F separation. Designated by 32 is an assaying reagent dispensing means for dispensing a measuring reagent into the reaction tubes T, and by 34 is an assaying means for assaying the amount of a labeling substance contained in a reaction solution subsequent to the reaction in the reaction tube T.

Reference numeral 36 denotes a rotating shaft rotatably supporting thereon the reaction tube turret 14. The rotating shaft 36 has a pulley 38 firmly attached thereto. Designated by 40 is an electric motor having a drive shaft 42 to which a motor pulley 44 is attached. The motor pulley 44 is connected with the pulley 38 via a timing belt 46 so that rotation of the motor pulley 44 is transmitted to the pulley 38 and thence to the rotating shaft 36 to intermittently rotate the reaction tube turret 14.

Figure 5:
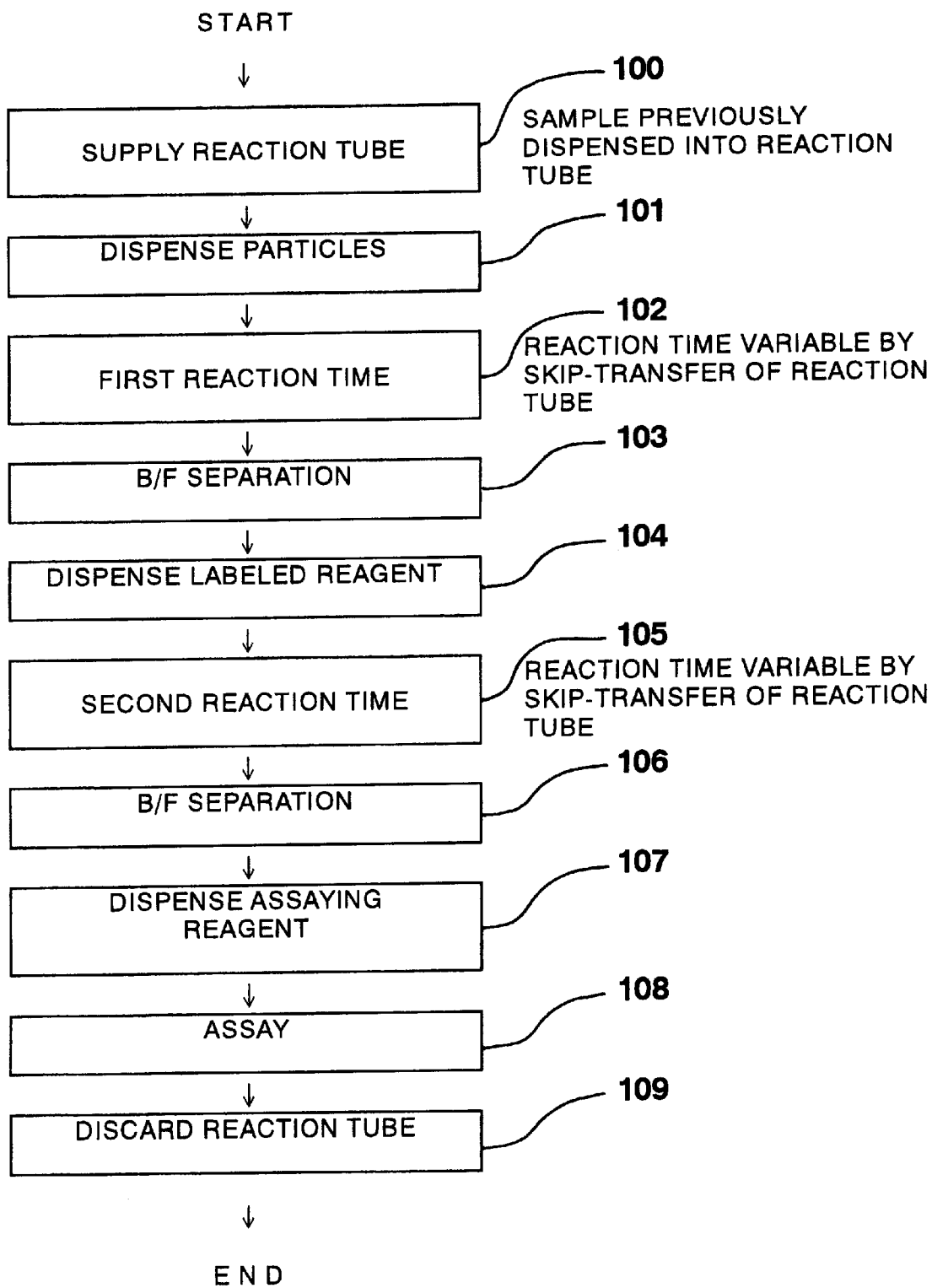
FIG. 5 is a flowchart showing one embodiment (two-step noncompetitive sandwich method) of an automatic immunoassay of the present invention.

The automatic immunoassay apparatus 12 of the foregoing construction is used for carrying out in various forms of an automatic immunoassays of the invention. One form of the immunoassays which is practiced or embodied in the two step noncompetitive sandwich method will be described below with reference to FIG. 5 showing a reaction flow, and with reference to FIGS. 6–17 showing the movement of reaction tubes T on the reaction tube turret 14.

At the beginning, a non-illustrated switch means is turned on whereupon the motor 40 of the automatic immunoassay apparatus 12 is driven to rotate the reaction tube turret 14 intermittently at a predetermined speed. With this intermittent rotation of the reaction tube turret 14, the reaction tube holders 16 angularly move along two parallel circular paths. The speed of intermittent rotation of the reaction tube turret 14 may be determined such that the turret 14 performs one of successive step like angular movements for each unit time, such as 30 seconds or 1 minute, selected in option according to the manner of reaction. In the illustrated embodiment, the turret is set to angularly move or turn through one unit angle per 30 seconds, as will be described below.

Figure 6:
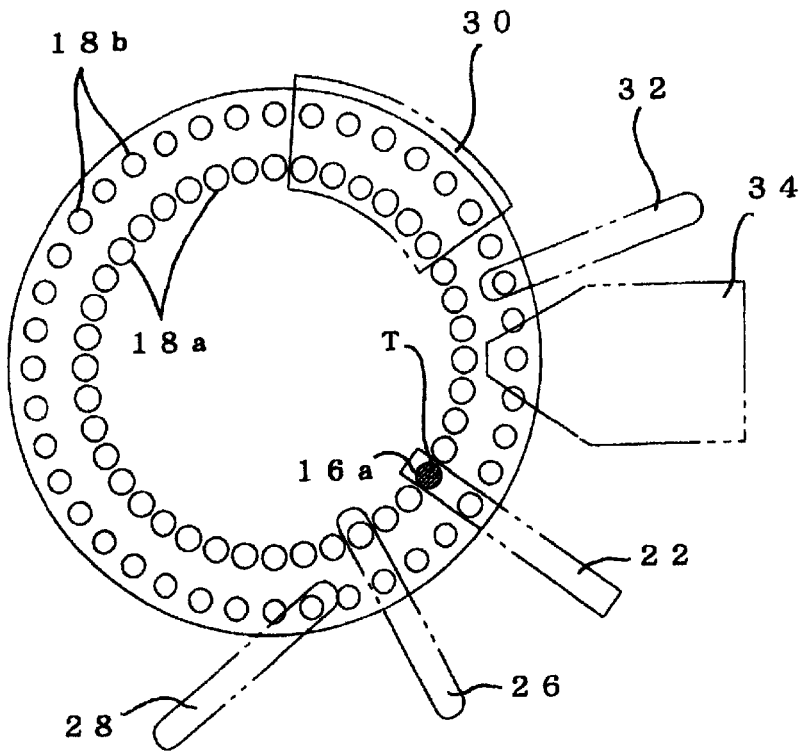
FIG. 6 is an explanatory view showing a first step of movement of reaction tubes on the reaction tube turret in the embodiment shown in FIG. 5.

At a step 100 (FIG. 5), the reaction tube supplying means incorporated in the reaction tube transfer means 22 supplies one reaction tube T at a time to a reaction tube holder 16a of the inner row 18a on the reaction tube turret 14 while the turret 14 continues its intermittent rotation (FIG. 6).

In this instance, the reaction tube T may hold or retain a sample supplied previously. Alternatively, the sample may be supplied after the reaction tube T is held in the reaction tube holder 16a. In the case of the illustrated embodiment, the sample is previously supplied to the reaction tube T.

Figure 7:
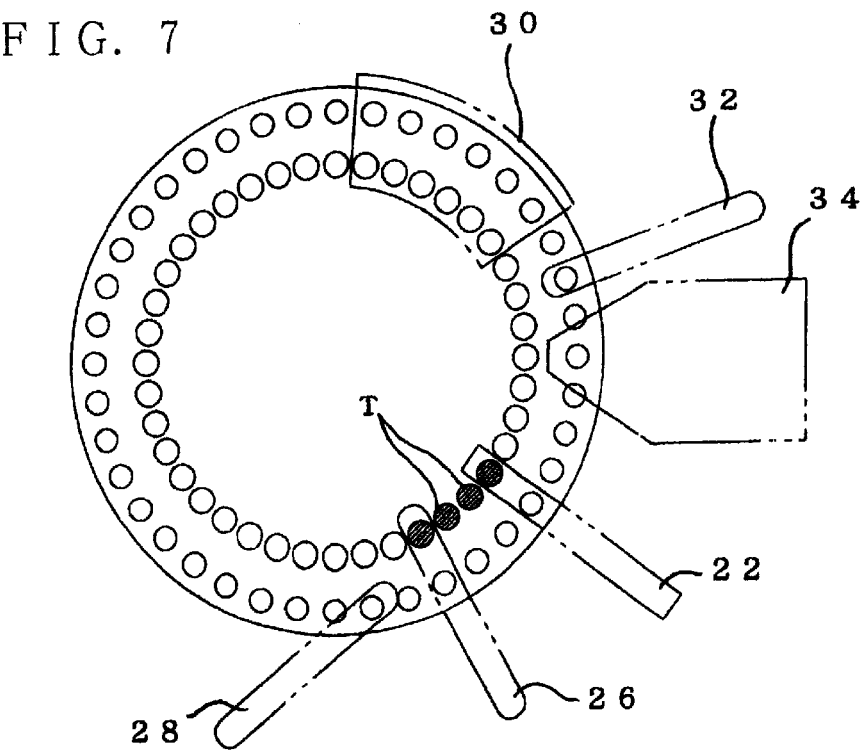
FIG. 7 is an explanatory view showing a second step of movement of the reaction tubes on the reaction tube turret in the embodiment shown in FIG. 5.
Figure 8:
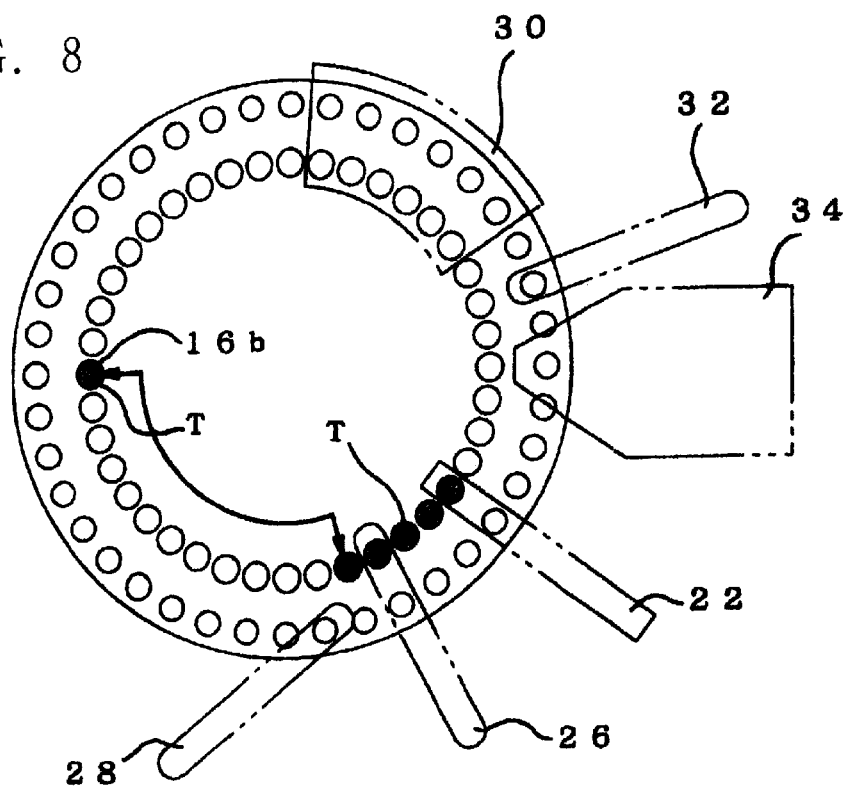
FIG. 8 is an explanatory view showing a third step of movement of the reaction tubes on the reaction tube turret in the embodiment shown in FIG. 5.

Then at a step 101, particles are supplied into the reaction tube T by the particle supplying means 26 (FIG. 7). The reaction tube T charged with the particles is transferred by the reaction tube transfer means 22 to a reaction tube holder 16 located at a predetermined position of the inner row 18a while skipping a predetermined number of successive reaction tube holders 16 according to a preset reaction time (5 minutes and 30 seconds in the illustrated embodiment). In the illustrated embodiment, the reaction tube T is transferred to a reaction tube holder 16b of the inner row 18a which is the eleventh reaction tube holder from the B/F separation means 30 with the result that the reaction time is set at 11×30 seconds=330 seconds (5 minutes and 30 seconds) (FIG. 8).

Figure 9:
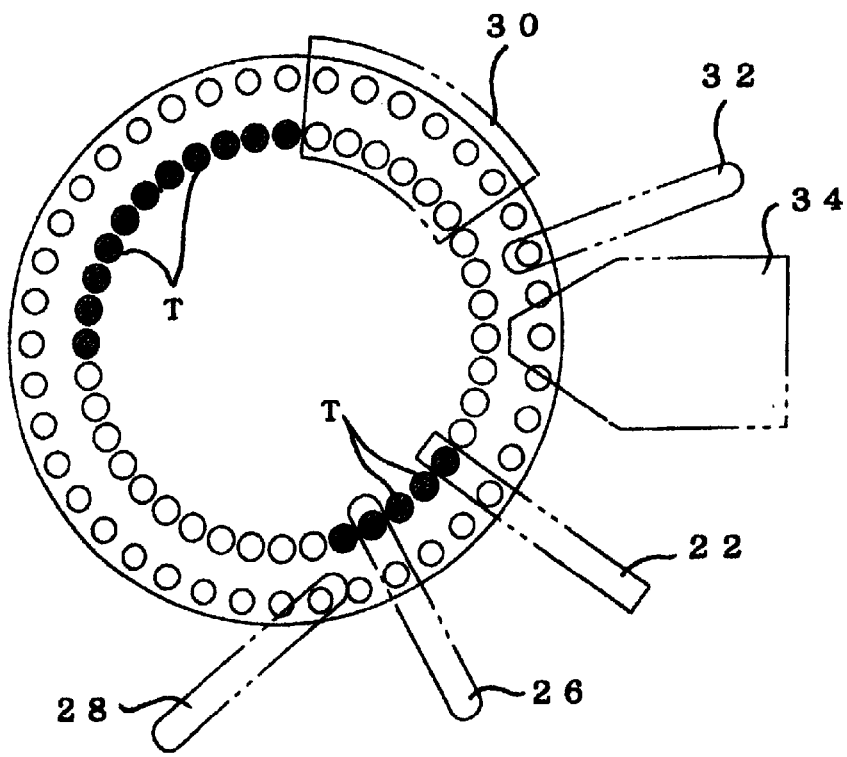
FIG. 9 is an explanatory view showing a fourth step of movement of the reaction tubes on the reaction tube turret in the embodiment shown in FIG. 5.

Thereafter, at a step 102, the sample and the particles take part in a first antigen-antibody reaction continuing for the predetermined period of time (FIG. 9).

Figure 10:
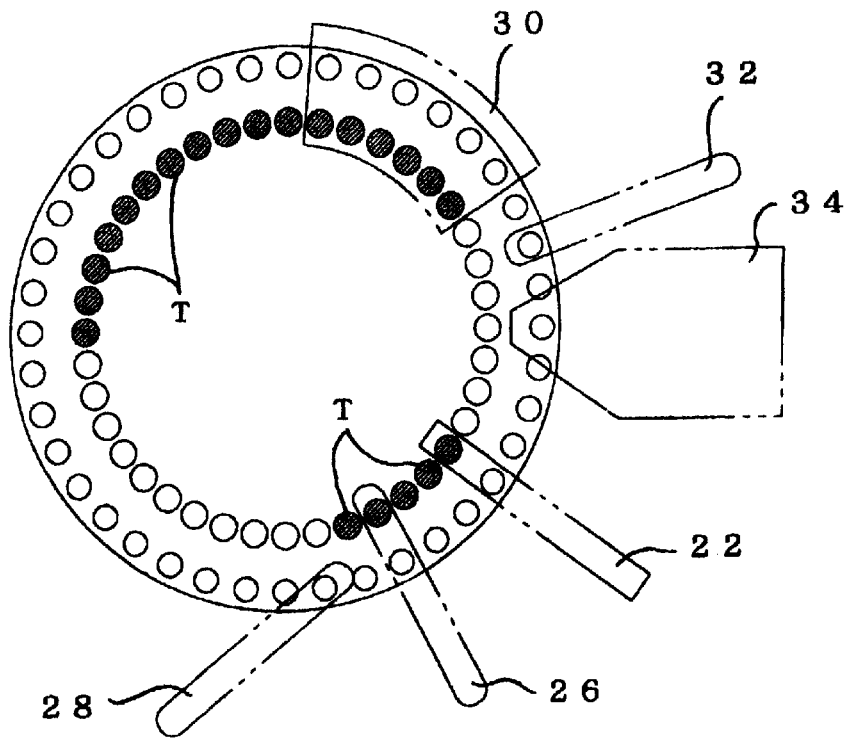
FIG. 10 is an explanatory view showing a fifth step of movement of the reaction tubes on the reaction tube turret in the embodiment shown in FIG. 5.
Figure 11:
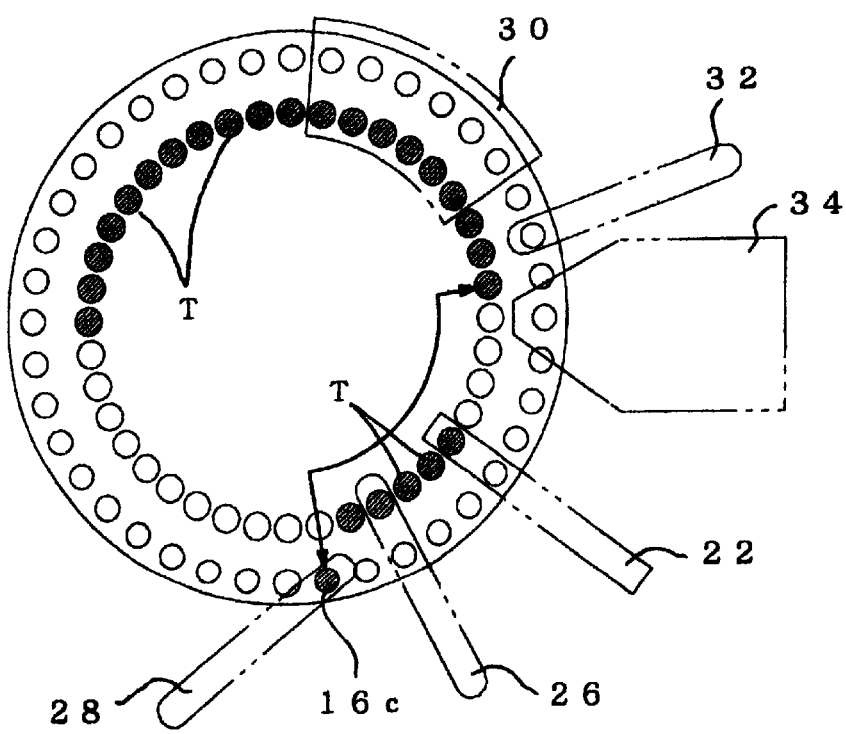
FIG. 11 is an explanatory view showing a sixth step of movement of the reaction tubes on the reaction tube turret in the embodiment shown in FIG. 5.

Then at a step 103, the particles, after the first reaction is completed, are sufficiently washed thereby to perform the B/F separation (FIG. 10). After the B/F separation, the reaction tube T is transferred by the reaction tube transfer means 22 to a reaction tube holder 16c located at a reagent dispensing position where the reagent dispensing means 28 is disposed (FIG. 11).

Figure 12:
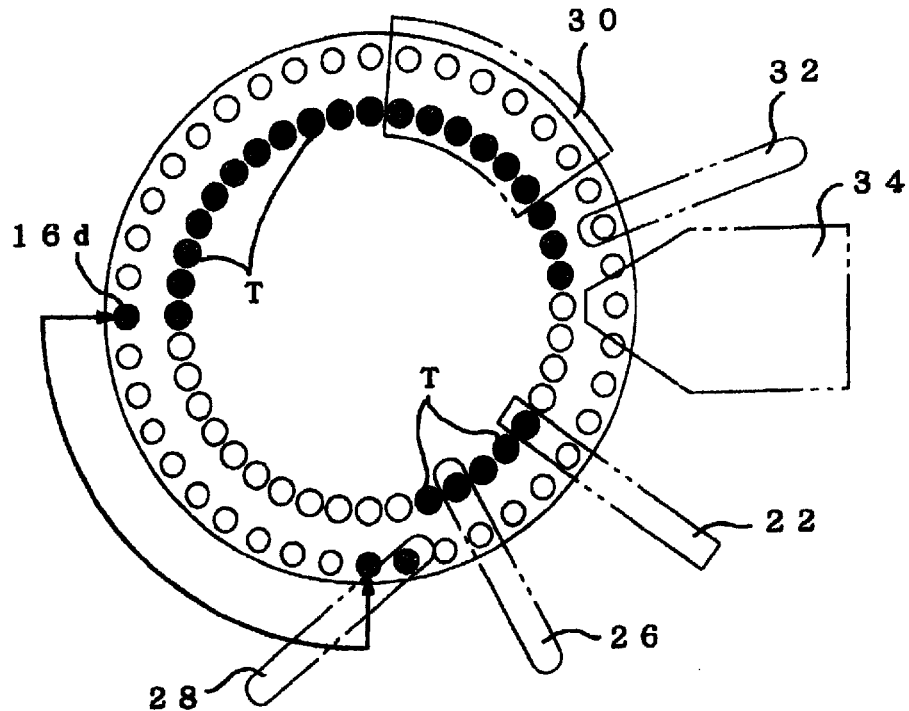
FIG. 12 is an explanatory view showing a seventh step of movement of the reaction tubes on the reaction tube turret in the embodiment shown in FIG. 5.

Subsequently at a step 104, a labeled reagent is dispensed from the reagent dispensing means 28 into the reaction tube T. The reaction tube T charged with the labeled reagent is then transferred again by the reaction tube transfer means 22 to the reaction tube holder 16 located at a predetermined position of the outer row 18b while skipping a predetermined number of successive reaction tube holders 16 according to a second preset reaction time (5 minutes and 30 seconds in the illustrated embodiment). In the illustrated embodiment, the reaction tube T is transferred to the eleventh reaction tube holder 16d in the outer row from the B/F separation means 30 with the result that the second reaction time is set at 11×30 seconds=330 seconds (5 minutes and 30 seconds) (FIG. 12).

Figure 13:
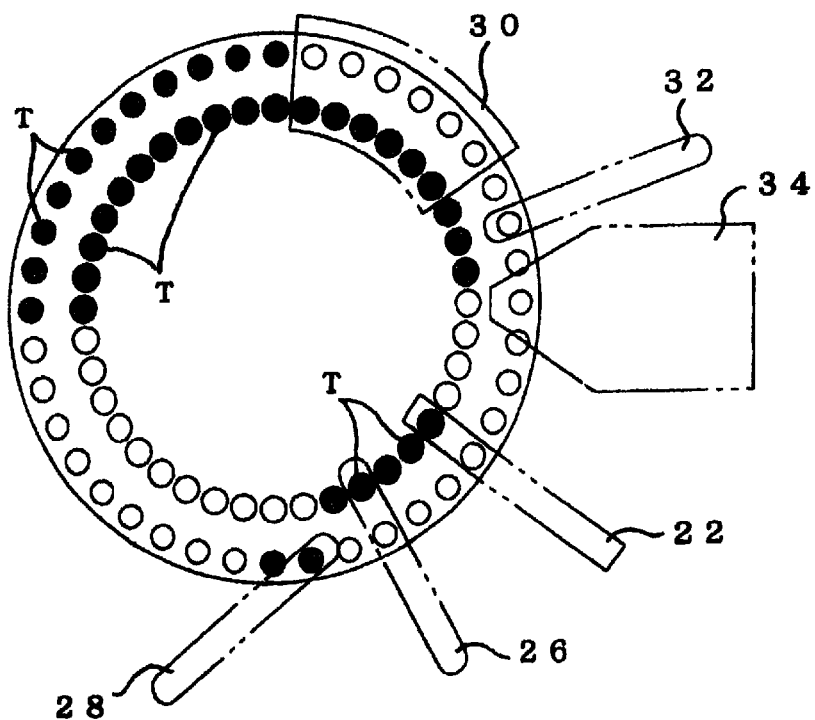
FIG. 13 is an explanatory view showing an eighth step of movement of the reaction tubes on the reaction tube turret in the embodiment shown in FIG. 5.

Then at a step 105, the sample, the particles and the labeled reagent take part in a second antigen-antibody reaction continuing for the predetermined period of time (FIG. 13).

Figure 14:
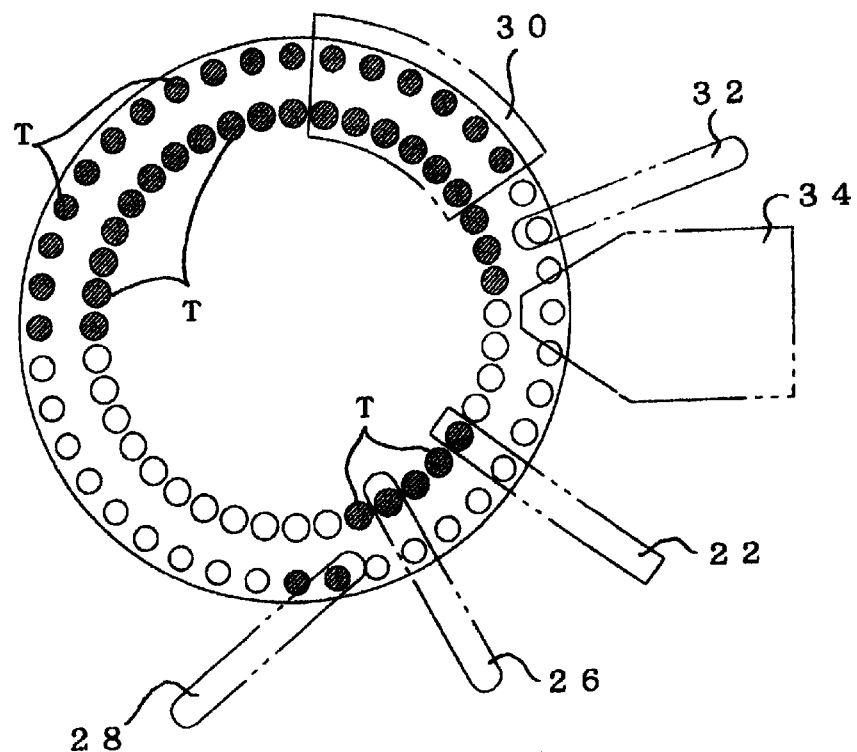
FIG. 14 is an explanatory view showing a ninth step of movement of the reaction tubes on the reaction tube turret in the embodiment shown in FIG. 5.

Thereafter, at a step 106, the particles, after the second reaction is completed, are sufficiently washed thereby to perform the B/F separation (FIG. 14).

Figure 15:
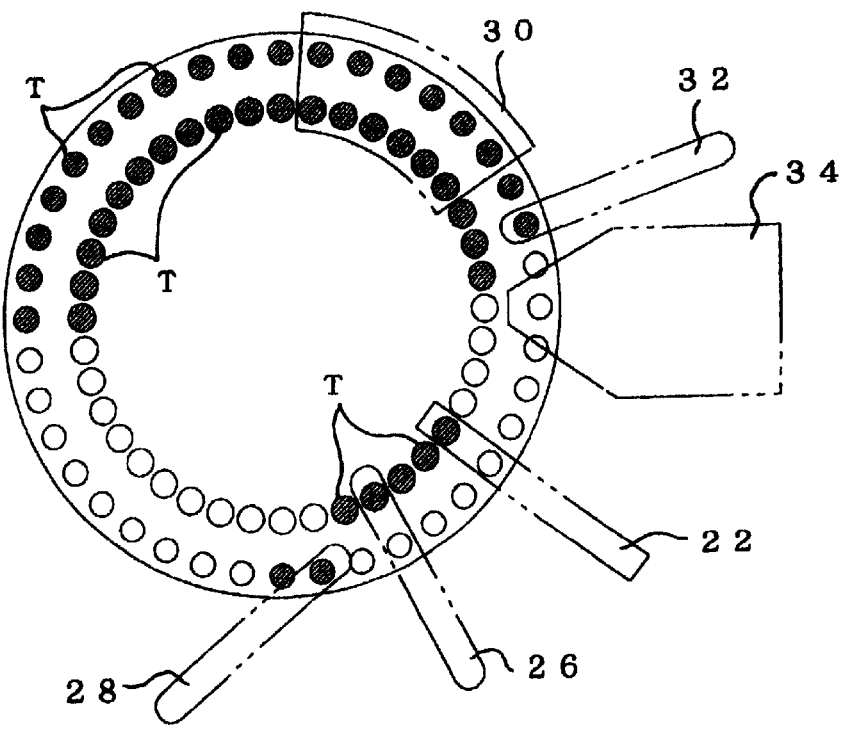
FIG. 15 is an explanatory view showing a tenth step of movement of the reaction tubes on the reaction tube turret in the embodiment shown in FIG. 5.

At a step 107, the reaction tube T after being subjected to the BIF separation is then supplied with a assaying reagent, such as a substrate, dispensed from the assaying reagent dispensing means 32 for assaying the amount of the labeling substance (FIG. 15).

Figure 16:
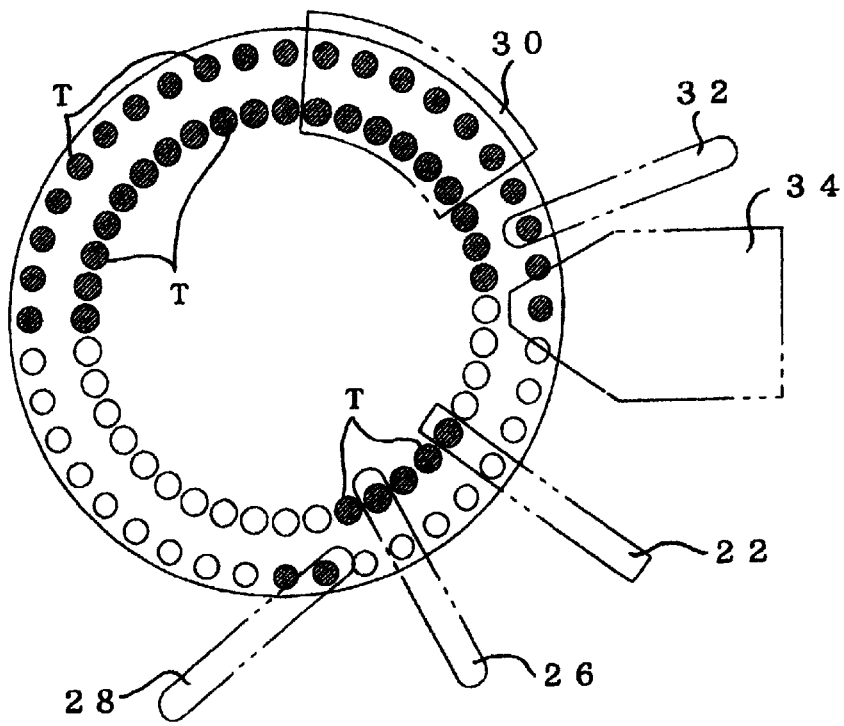
FIG. 16 is an explanatory view showing a ninth step of movement of the reaction tubes on the reaction tube turret in the embodiment shown in FIG. 5.

Then at a step 108, the amount of the labeling substance in the reacted reaction solution held in the reaction tube T is assayed (FIG. 16). For this asssay, a colorimetric assay is performed, in general, by making use of the property of the reaction solution which exhibits a colorational phenomenon, a fluorescent phenomenon, or a chemiluminescent phenomenon as soon as the assaying reagent is dispensed.

Figure 17:
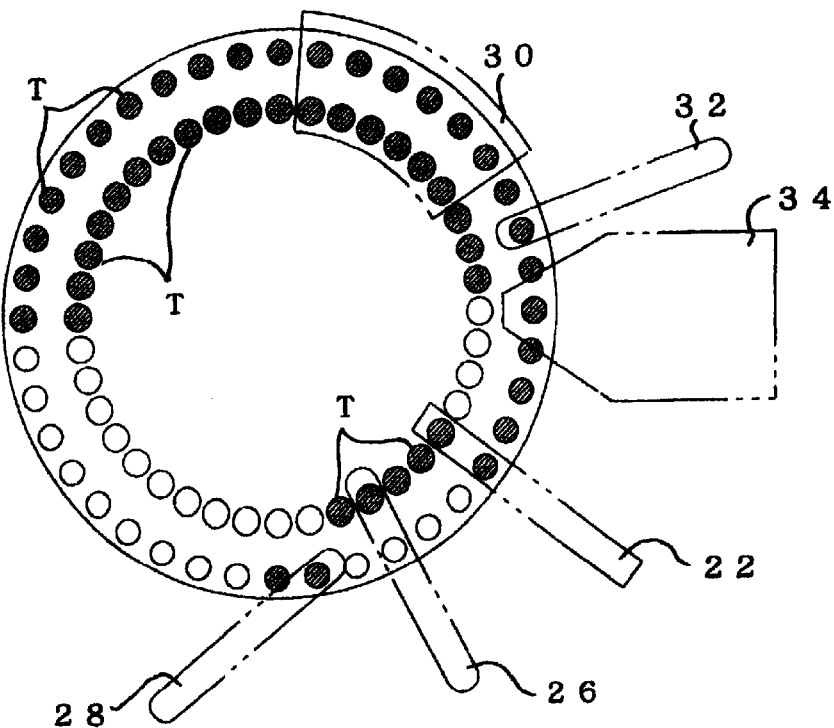
FIG. 17 is an explanatory view showing a tenth step of movement of the reaction tubes on the reaction tube turret in the embodiment shown in FIG. 5.
Figure 18:
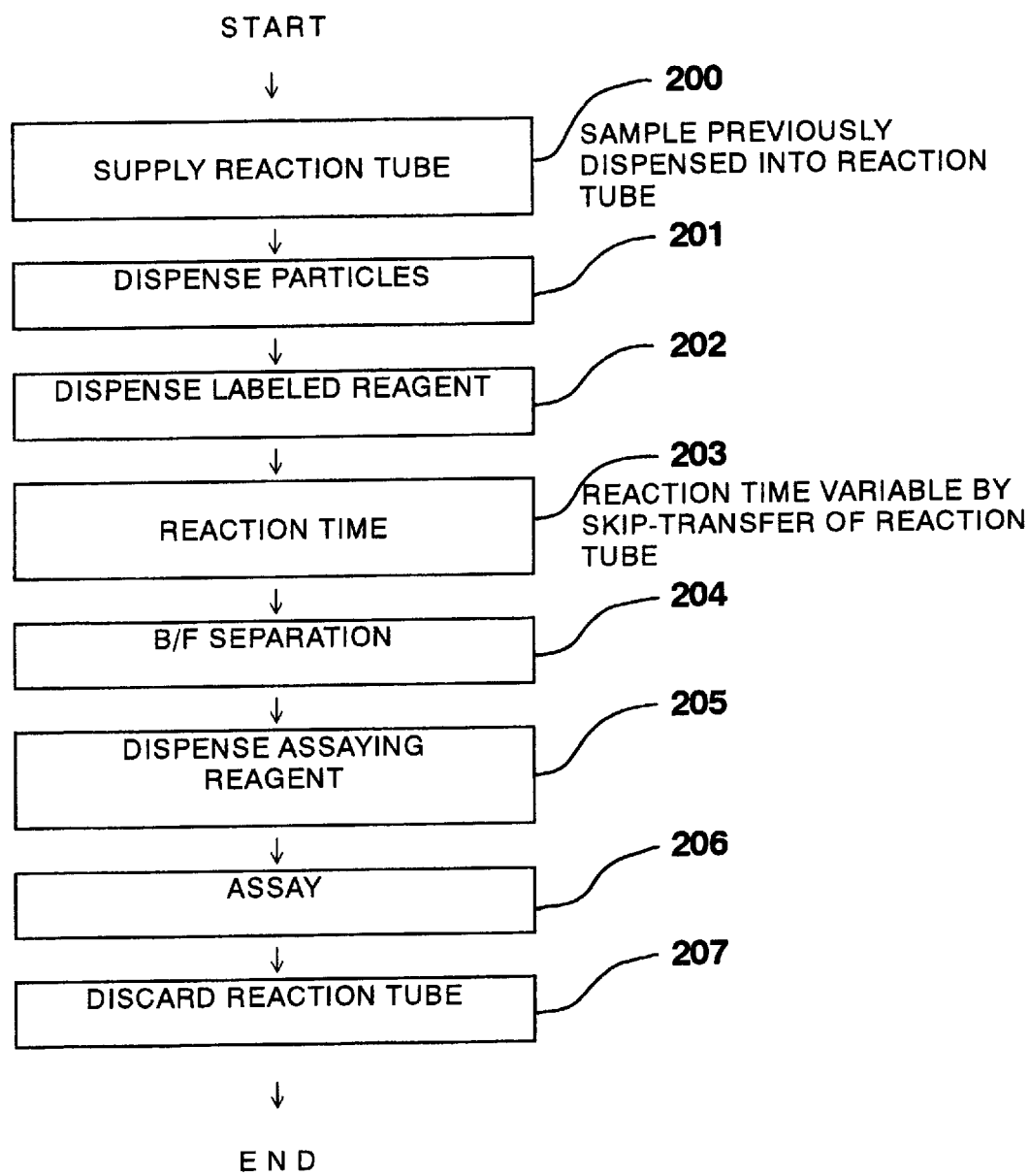
FIG. 18 is a flowchart showing another embodiment (one-step noncompetitive sandwich method using an outer row of reaction tube holders only) of the method of the present invention.

Finally at a step 109, the reaction tube discarding means incorporated in the reaction tube transfer means 22 discards the assayed reaction tube T (FIG. 17).

Now, another embodiment of the present invention which is embodied in the one-step noncompetitive sandwich method by making use of only the outer row 18b of reaction tube holders of the reaction tube turret 14 will be described below with reference to FIG. 18 and FIGS. 18–26 showing a reaction flow, and movements of reaction tubes T on the reaction tube turret 14, respectively. For these operations which are the same as those shown in FIGS. 6–17, description can be omitted.

At first, a non-illustrated switch means is turned on whereupon the automatic immunoassay apparatus 12 is energized in the same manner as the foregoing embodiment. Thus, the reaction tube turret 14 is intermittently rotated at a predetermined speed, and with this intermittent rotation of the reaction tube turret 14, the reaction tube holders 16 angularly move along two parallel circular paths. In this embodiment, the speed of intermittent rotation of the reaction tube turret 14 is also set such that the turret 14 performs one of successive steplike angular movements for each unit time of 30 seconds.

Figure 19:
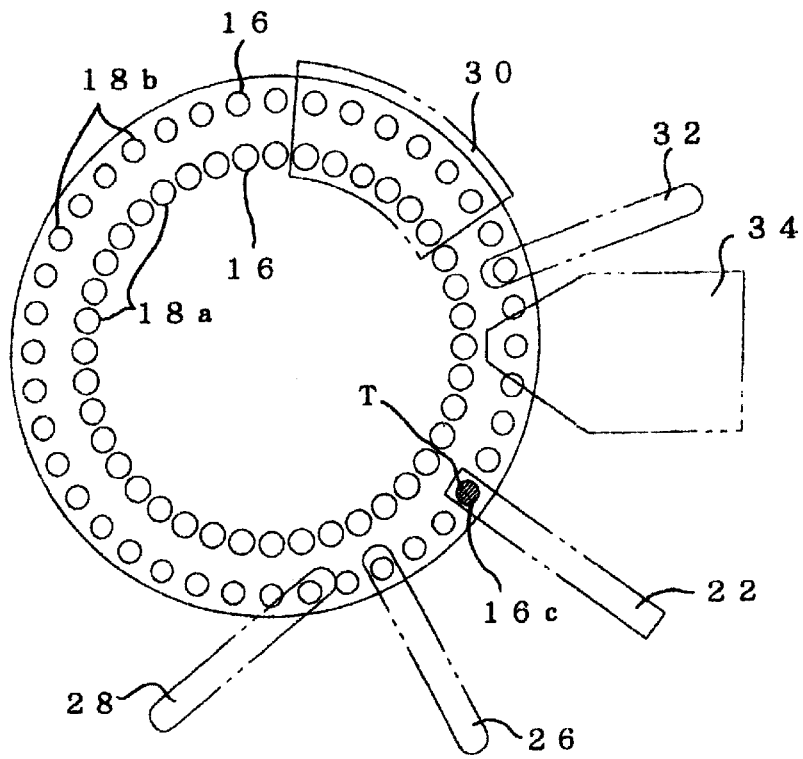
FIG. 19 is an explanatory view showing a first step of movement of reaction tubes on the reaction tube turret in the embodiment shown in FIG. 18.

At a step 200 (FIG. 18), the reaction tube supplying means incorporated in the reaction tube transfer means 22 supplies one reaction tube T at a time to a reaction tube holder 16e of the outer row 18b on the reaction tube turret 14 while the turret 14 continues its intermittent rotation (FIG. 19).

In this instance, a sample may be supplied to the reaction tube T either before or after the same reaction tube T is held in the reaction tube holder 16d. In the illustrated embodiment, the sample is previously dispensed to the reaction tube T.

Figure 20:
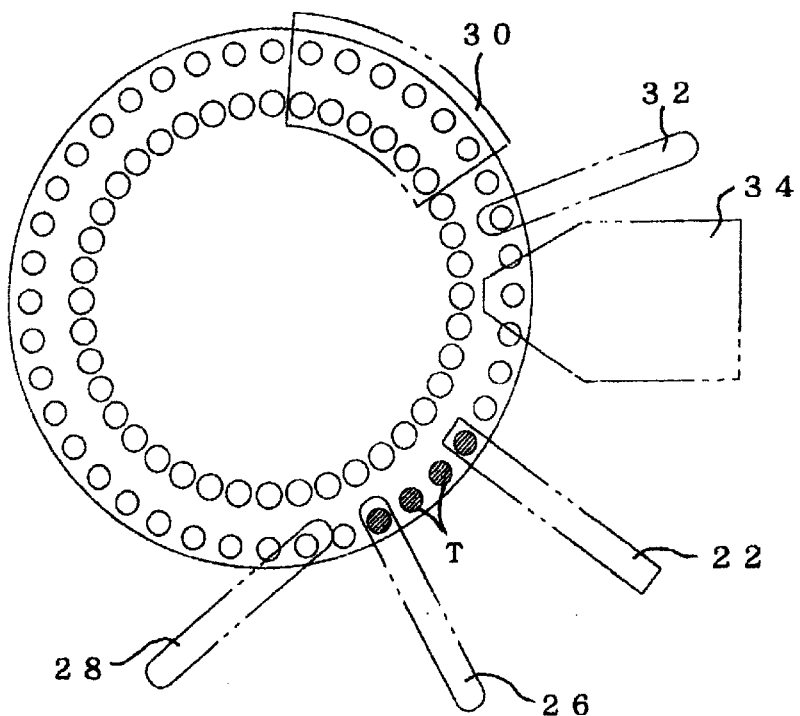
FIG. 20 is an explanatory view showing a second step of movement of the reaction tubes on the reaction tube turret in the embodiment shown in FIG. 18.

Then at a step 201, the particle supplying means 26 supplies particles into the reaction tube T (FIG. 20).

Figure 21:
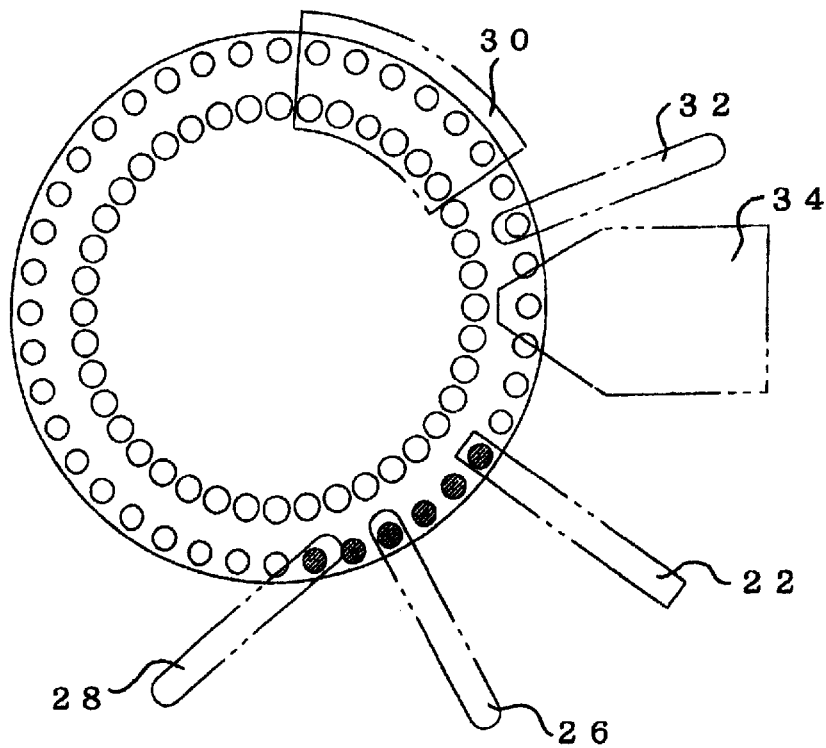
FIG. 21 is an explanatory view showing a third step of movement of the reaction tubes on the reaction tube turret in the embodiment shown in FIG. 18.
Figure 22:
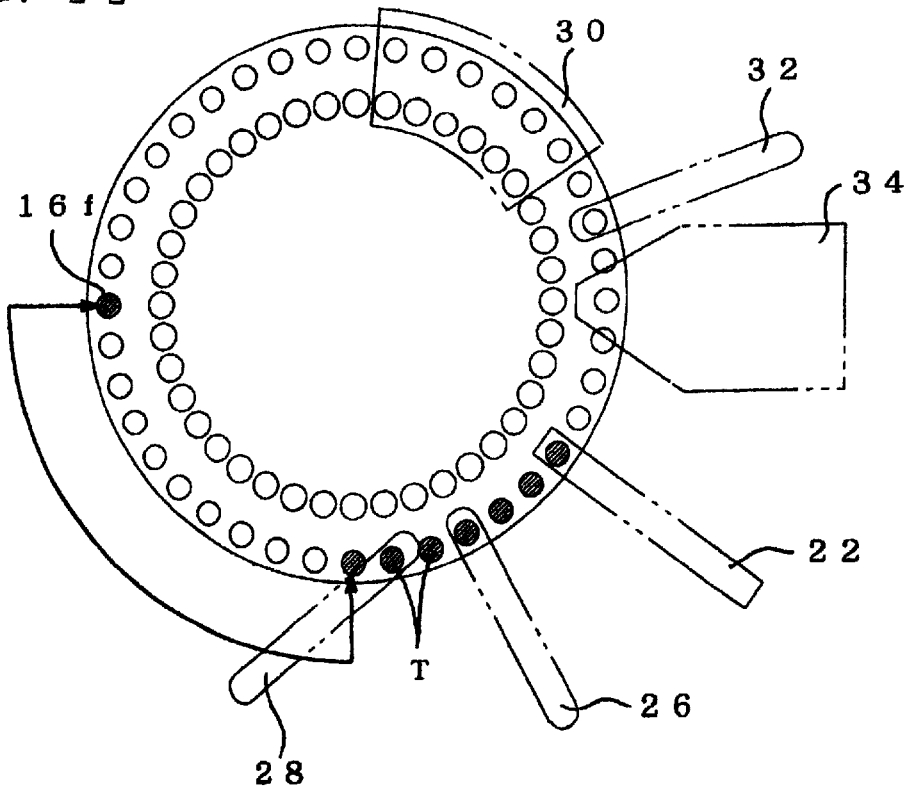
FIG. 22 is an explanatory view showing a fourth step of movement of the reaction tubes on the reaction tube turret in the embodiment shown in FIG. 18.

Thereafter, at a step 202, the reagent dispensing means 28 supplies a labeled reagent into the reaction tube T (FIG. 21). The reaction tube T charged with the particles and the labeled reagent is then transferred by the reaction tube transfer means 22 to the reaction tube holder 16 located at a predetermined position of the outer row 18b while skipping a predetermined number of successive reaction tube holders 16 according to a preset reaction time (5 minutes and 30 seconds in the illustrated embodiment) (FIG. 22). In this embodiment, the reaction tube T is transferred to the reaction tube holder 16f of the outer row 18b which is the eleventh reaction tube holder from the B/F separation means 30 with the result that the reaction time is set at 11×30 seconds=330 seconds (5 minutes and 30 seconds) (FIG. 22).

Figure 23:
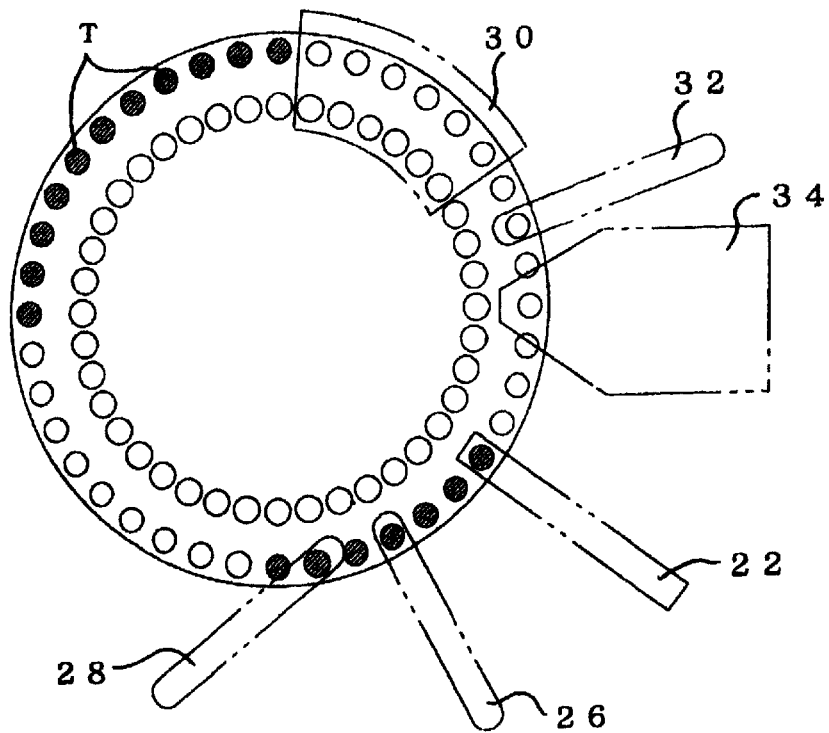
FIG. 23 is an explanatory view showing a fifth step of movement of the reaction tubes on the reaction tube turret in the embodiment shown in FIG. 18.

Then at a step 203, the sample, the particles and the reagent react with each other to perform an antigen-antibody reaction continuing for the predetermined period of time (FIG. 23).

Figure 24:
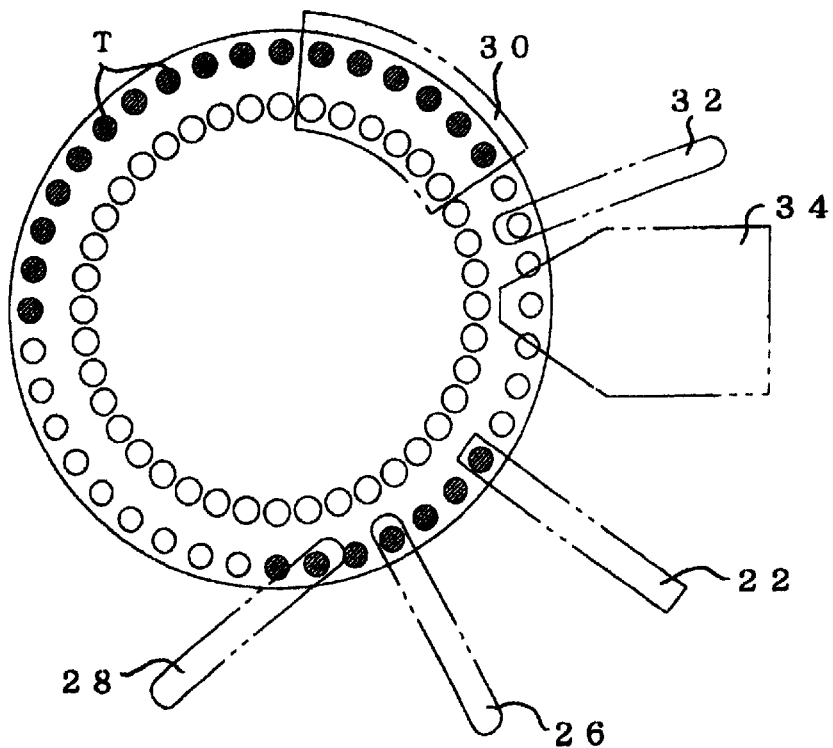
FIG. 24 is an explanatory view showing a sixth step of movement of the reaction tubes on the reaction tube turret in the embodiment shown in FIG. 18.

At a step 204, the particles, after the reaction, are sufficiently washed thereby to perform the B/F separation (FIG. 24).

Figure 25:
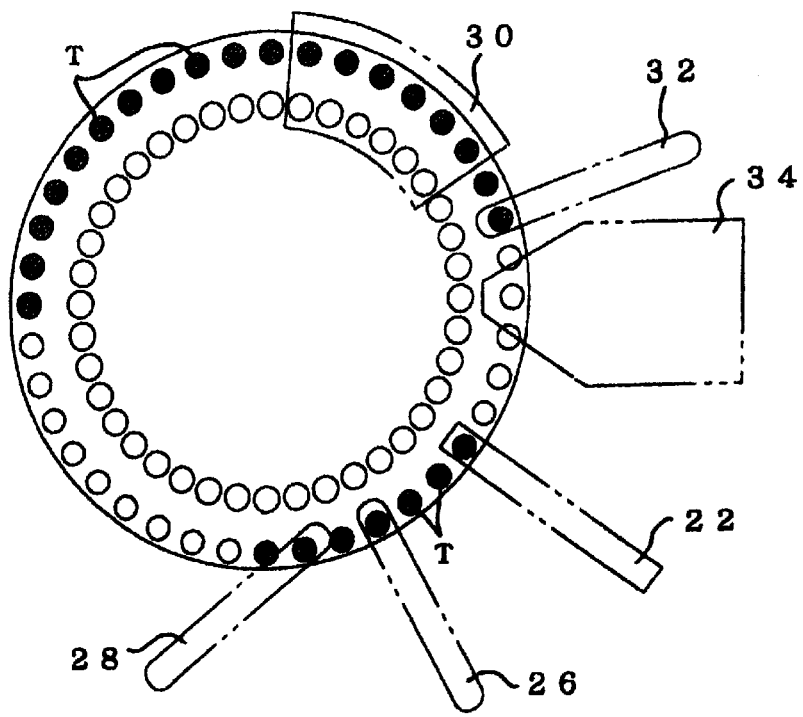
FIG. 25 is an explanatory view showing a seventh step of movement of the reaction tubes on the reaction tube turret in the embodiment shown in FIG. 18.

Subsequently at a step 205, the reaction tube T after being subjected to the B/F separation is then supplied with an assaying reagent, such as a substrate, dispensed from the assaying reagent dispensing means 32 for the assay of the amount of the labeling substance (FIG. 25).

Figure 26:
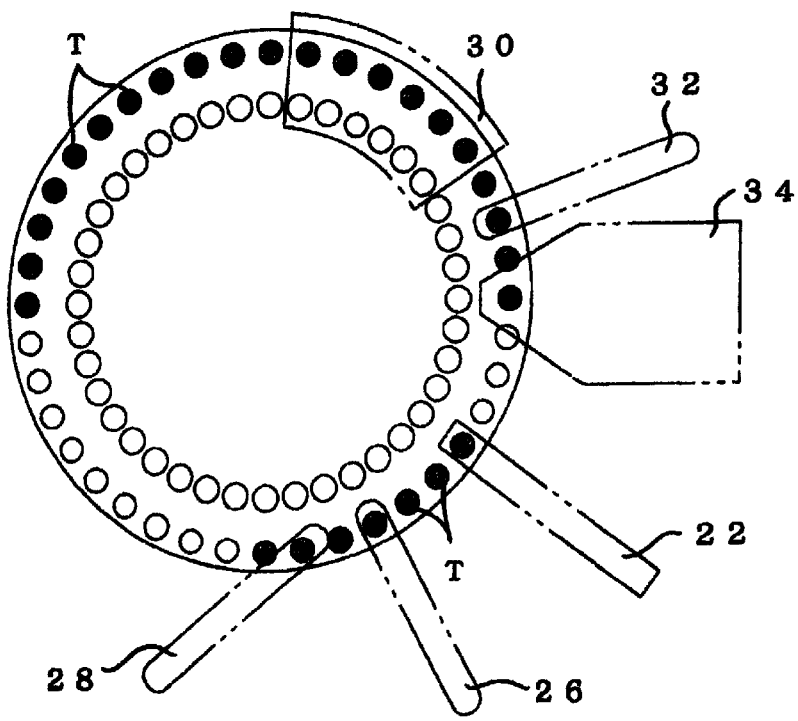
FIG. 26 is an explanatory view showing an eighth step of movement of the reaction tubes on the reaction tube turret in the embodiment shown in FIG. 18.

Then at a step 206, the amount of the labeling substance in the reacted reaction solution held within the reaction tube T is assayed (FIG. 26). For this assay, a colorimetric assay is performed, in general, by making use of the property of the reaction solution which exhibits a colorational phenomenon, a fluorescent phenomenon, or a chemiluminescent phenomenon as soon as the assaying reagent is dispensed.

Figure 27:
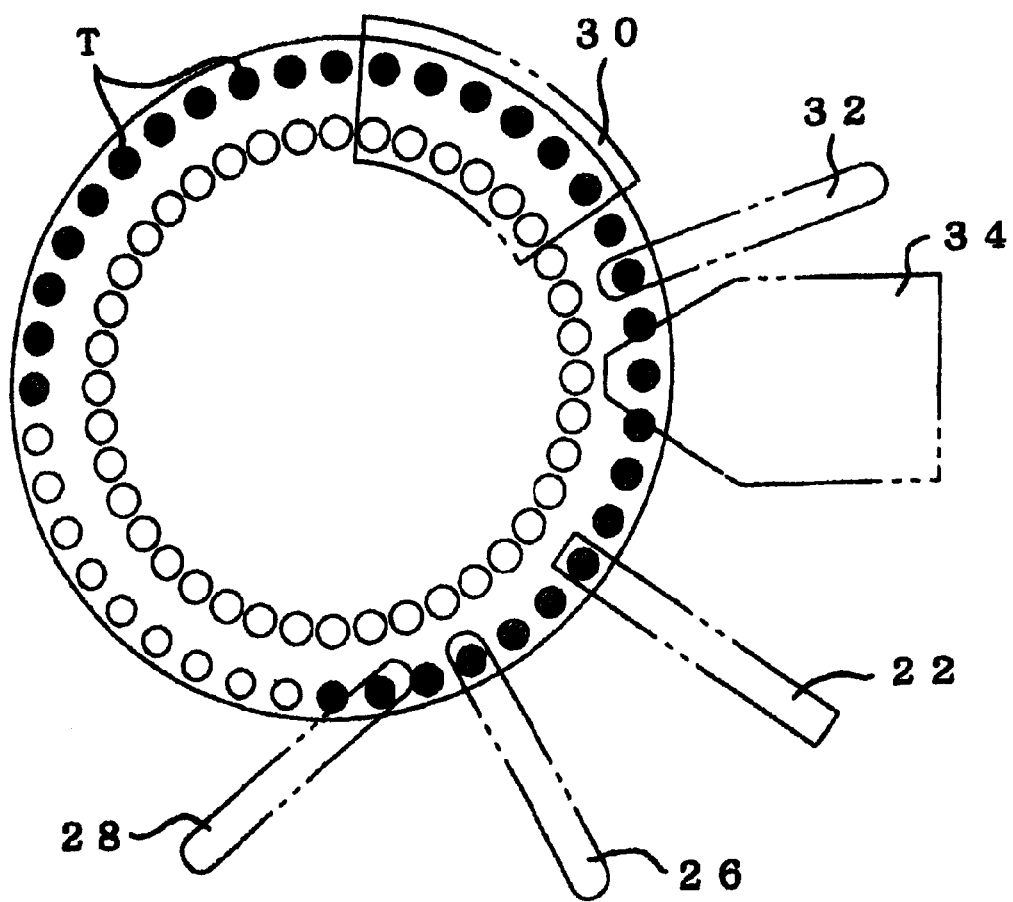
FIG. 27 is an explanatory view showing a ninth step of movement of the reaction tubes on the reaction tube turret in the embodiment shown in FIG. 18.
Figure 28:
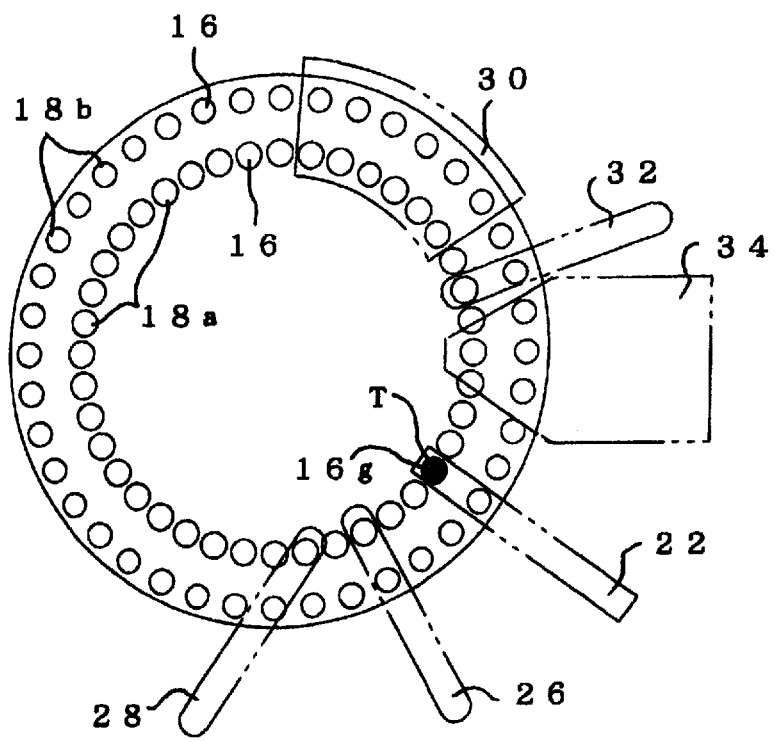
FIG. 28 is an explanatory view showing a first step of movement of reaction tubes on the reaction tube turret according to a further embodiment (one-step noncompetitive sandwich method using an outer row of reaction tube holders only) of the method of the present invention.
Figure 29:
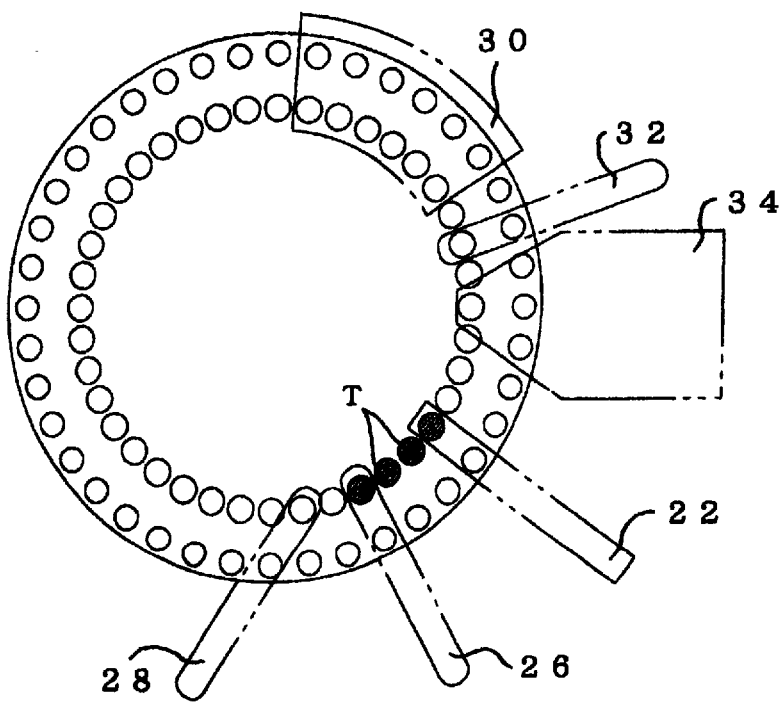
FIG. 29 is an explanatory view showing a second step of movement of the reaction tubes on the reaction tube turret in said further embodiment.
Figure 30:
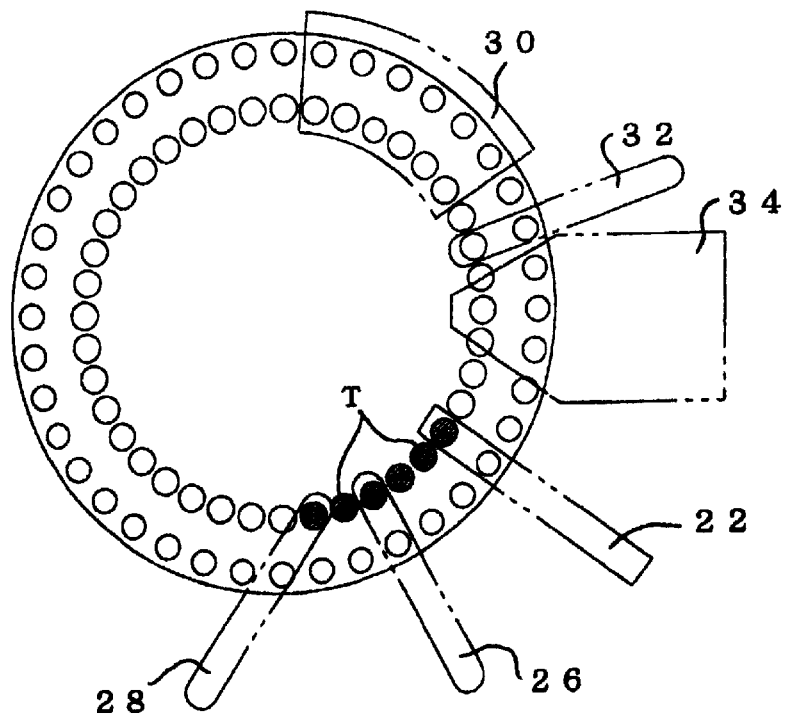
FIG. 30 is an explanatory view showing a third step of movement of the reaction tubes on the reaction tube turret in said further embodiment.
Figure 31:
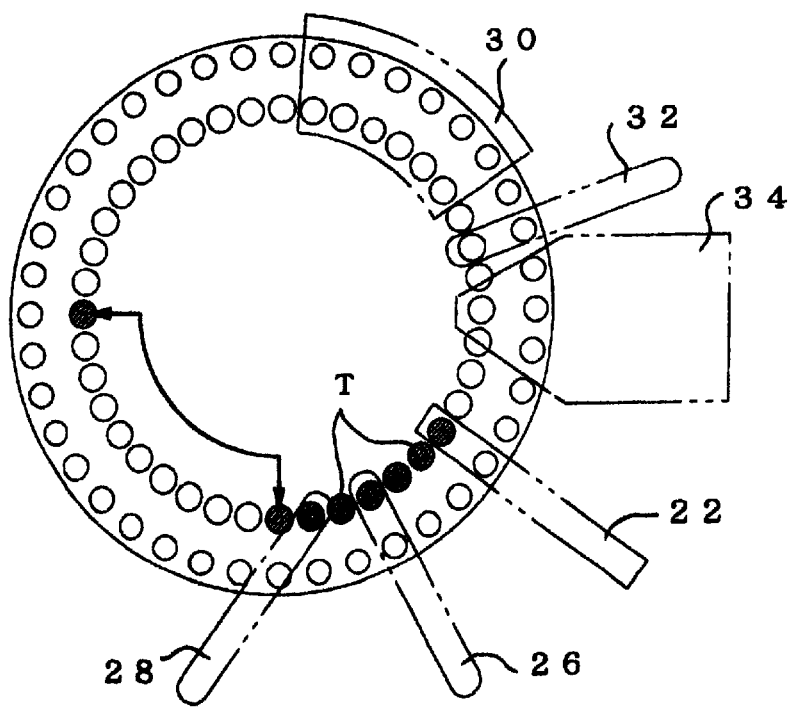
FIG. 31 is an explanatory view showing a fourth step of movement of the reaction tubes on the reaction tube turret in said further embodiment.
Figure 32:
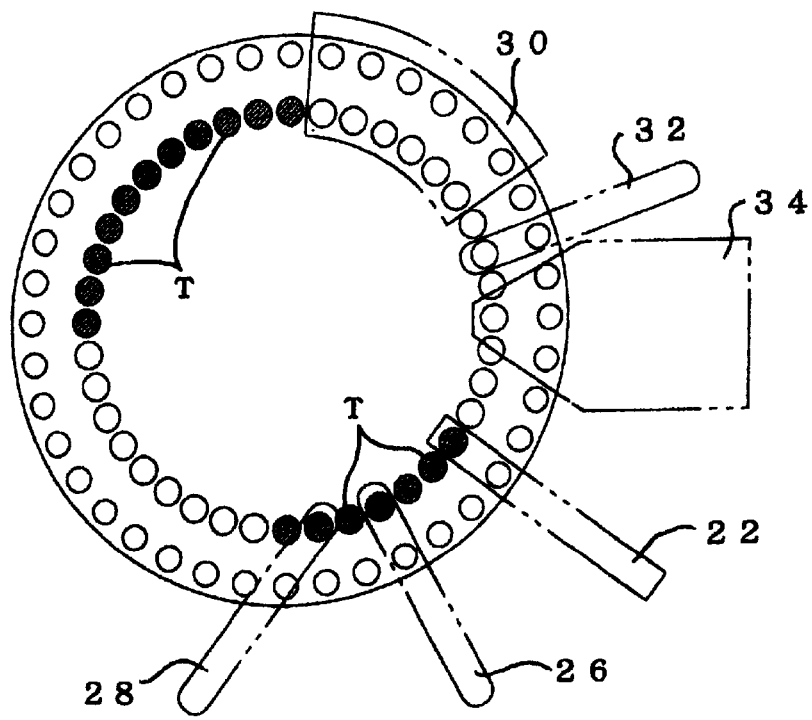
FIG. 32 is an explanatory view showing a fifth step of movement of the reaction tubes on the reaction tube turret in said further embodiment.
Figure 33:
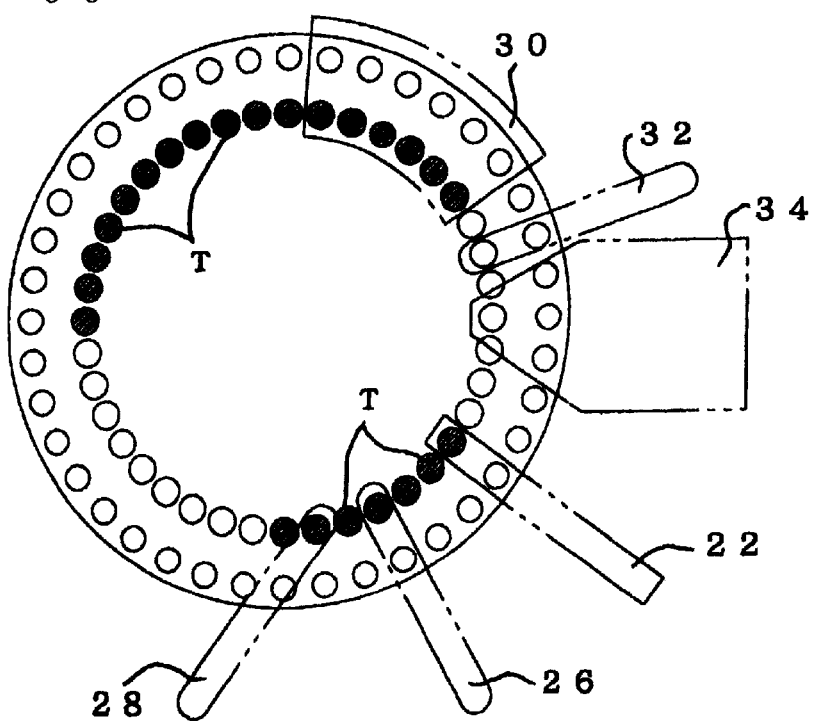
FIG. 33 is an explanatory view showing a sixth step of movement of the reaction tubes on the reaction tube turret in said further embodiment.
Figure 34:
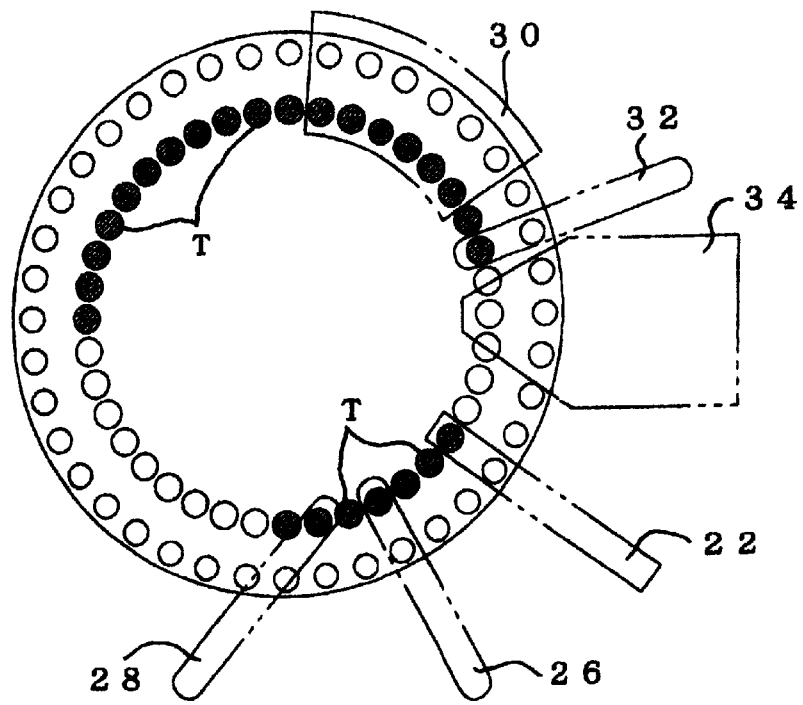
FIG. 34 is an explanatory view showing a seventh step of movement of the reaction tubes on the reaction tube turret in said further embodiment.
Figure 35:
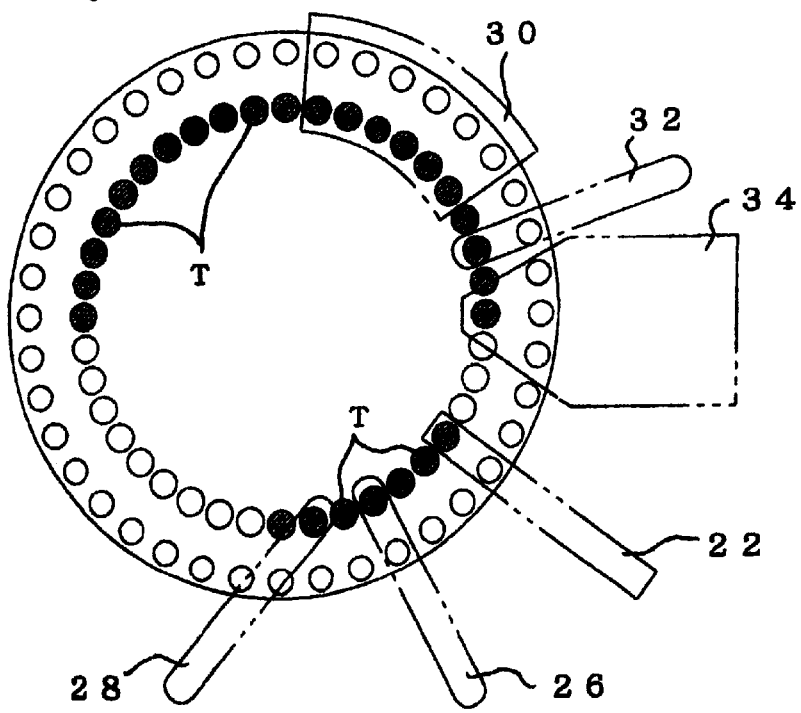
FIG. 35 is an explanatory view showing an eighth step of movement of the reaction tubes on the reaction tube turret in said further embodiment.
Figure 36:
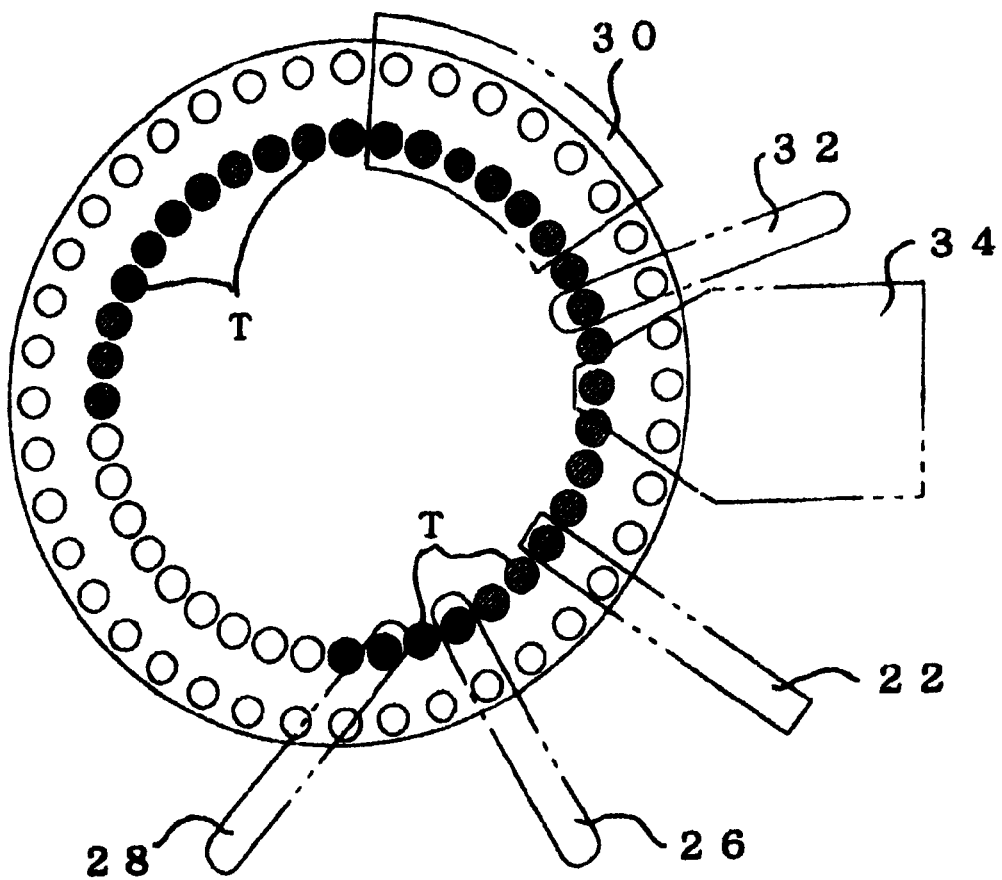
FIG. 36 is an explanatory view showing a ninth step of movement of the reaction tubes on the reaction tube turret in said further embodiment.

Finally at a step 207, the reaction tube discarding means incorporated in the reaction tube transfer means 22 discards the assayed reaction tube T (FIG. 27).

According to the embodiment just described above in conjunction with the one step noncompetitive sandwich method, the reaction tubes T are supplied to the outer row of reaction tube holders at the position indicated by 16e and, thereafter, successive operations are performed during which time only the reaction tube holders of the outer row are used. Alternatively, as shown in FIGS. 28–36, the reaction tubes T may be supplied to the inner row of reaction tube holders at the position indicated by 16g, and subsequent processing operations are performed while using the inner row of reaction tube holders alone, in the same manner as shown in FIGS. 19–25. Furthermore, if necessary, an operation may be performed such that the reaction tubes T are supplied to the reaction tube holders of the inner row, then the operation proceeds with while using the inner row of reaction tube holders until after the labeled reagent is dispensed, and after that the reaction tubes T are transferred by the reaction tube transfer means 22 to the reaction tube holders of the outer row while skipping a predetermined number of reaction tube holders so that the reaction between the sample, the particles and the labeled reagent takes place in the reaction tubes held in the reaction tube holders of the outer row.

Although in the embodiments described herein, the invention is practiced in the one step or two step noncompetitive sandwich method, the invention may be embodied in the competitive method in the same manner as the one step noncompetitive method described herein. In any form of application to the foregoing assaying methods or techniques, the present invention makes it possible to set a desired reaction time by appropriately using one or both of the inner and outer rows of reaction tube holders. In setting the reaction time, the number of reaction tube holders 16 provided in each row on the reaction tube turret 14 is used to determine a desired arrival position of the reaction tubes to be skip-transferred by the reaction tube transfer means. This makes it possible to set various reaction times with high degree of flexibility.

CAPABILITY OF EXPLOITATION IN INDUSTRY

As described above, according to the present invention, various operations required, in performing an immunoassay, for supplying and discarding the reaction tube, for washing for the B/F separation, for dispensing a reagent, and for an assay, can be achieved automatically. In addition, the reaction time can be changed freely. The present invention can, therefore, be readily practiced and embodied in various assaying techniques including the one step or two step noncompetitive sandwich method, and the competitive method.

What is claimed is:

1. An automatic immunoassay apparatus comprising:
- a reaction tube turret that rotates intermittently at a predetermined speed;
- a reaction tube holding portion including a plurality of reaction tube holders arranged in two rows composed of an inner row and an outer row along the periphery of an upper surface of said reaction tube turret;
- a reaction tube supplying means for supplying a reaction tube to and from a predetermined one of said reaction tube holders of said reaction tube holding portion;
- a reaction tube transfer means for transferring the reaction tube held by one of said reaction tube holders to another reaction tube holder while skipping a desired number of reaction tube holders;
- a sample dispensing means for dispensing a sample to the reaction tube;
- a particle supplying means for supplying particles to the reaction tube;
- a reagent dispensing means for dispensing a labeled reagent to the reaction tube;
- a washing means for separating bound particles from free particles;
- an assay reagent dispensing means for dispensing an assaying reagent to the reaction tube;
- an assaying means for assaying the amount of the labeling substance in a reacted reaction solution in the reaction tube; and
- a reaction tube discarding means for removing the assayed reaction tube from said reaction tube holding portion and discarding the thus removed reaction tube.

2. The automatic immunoassay apparatus according to claim 1 wherein said inner and outer rows each have thirty reaction tube holders.

3. The automatic immunoassay apparatus according to claim 1 wherein said reaction tube transfer means comprises an X-axis transfer mechanism that transfers the reaction tube in a first direction relative to the apparatus and a Y-axis means that transfer the reaction tube in a second direction orthogonal to the first direction.

4. The automatic immunoassay apparatus according to claim 1, further comprising a rotating shaft having a first end and a second end, the first end of the rotation shaft rotatable supports said turret and said second end has a first pulley attached thereto.

5. The automatic immunoassay apparatus according to claim 4, further comprising an electric motor having a drive shaft, wherein a second pulley is attached to said drive shaft and connected to said first pulley by a timing belt, and wherein any rotation of said second pulley is transmitted to said rotating shaft via said first pulley to intermittently rotate said turret.

* * * * *

UNITED STATES PATENT AND TRADEMARK OFFICE
CERTIFICATE OF CORRECTION

PATENT NO. : 6,103,193

DATED : August 15, 2000

INVENTOR(S) : Iwahashi, et al.

It is certified that error appears in the above-identified patent and that said Letters Patent is hereby corrected as shown below:

On the title page,

Item [54], please delete --AUTOMATIC IMMUNOASSAY METHOD AND APPARATUS--, and insert --METHOD AND APPARATUS FOR AUTOMATIC IMMUNOASSAY.

Signed and Sealed this

Twenty-ninth Day of May, 2001

*Attest:*

NICHOLAS P. GODICI

*Attesting Officer*    *Acting Director of the United States Patent and Trademark Office*